United States Patent [19]

Olney et al.

[11] Patent Number: 5,605,911
[45] Date of Patent: Feb. 25, 1997

[54] USE OF ALPHA-2 ADRENERGIC DRUGS TO PREVENT ADVERSE EFFECTS OF NMDA RECEPTOR HYPOFUNCTION (NRH)

[75] Inventors: John W. Olney, Ladue; Nuri B. Farber, University City, both of Mo.

[73] Assignee: Washington University, St. Louis, Mo.

[21] Appl. No.: 381,334

[22] Filed: Jan. 31, 1995

[51] Int. Cl.$^6$ .................. A61K 31/54; A61K 31/445
[52] U.S. Cl. .................................................. 514/315
[58] Field of Search ........................ 514/315, 226.2, 514/318, 646

[56] References Cited

U.S. PATENT DOCUMENTS 5,034,400  7/1991  Olney ......................................... 514/315

OTHER PUBLICATIONS

Farber, N. B., et al, "Antipsychotic drugs block phencyclidine receptor–mediated neurotoxicity," *Biol Psychiatry* 34: 119–121 (1993).
Freedman, R., et al, "Clonidine treatment of schizophrenia: Double–blind comparison to placebo and neuroleptic drugs," *Acta Psych. Scand.* 65: 35–40 (1982).
Jimerson, D. C., et al, "Preliminary trial of the noradrenergic agonist clonidine in psychiatric patients," Biol. Psychiatry 14: 45–57 (1980).
Ko, G. N., et al, "Alpha–2 adrenergic agonist binding in Schizophrenic brains," *Psychopharmacology Bulletin* 22: 1011–1016 (1986).
Olney, J. W., et al, "NMDA antagonist neurotoxicity: Mechanism and prevention," *Science* 254: 1515–1518 (1991).
Rogawski, M. A., "The NMDA receptor, NMDA antagonists, and epilepsy therapy: A status report," *Drugs* 44: 279–292 (1992).
Ruffolo, R. R., et al, "Pharmacologic and therapeutic applications of α2–adrenoceptor subtypes," Annu. Rev. *Pharmacol. Toxicol.* 32: 243–279 (1993).
Trendelenburg, A., et al, "Presynaptic a2 autoreceptors in brain cortex: α2D in the rat and α2A in the rabbit," *Arch Pharmacol* 348: 35–45 (1993).
Van Kammen, D. P., et al, "Clonidine treatment of schizophrenia: Can we predict treatment response?" *Psychiatry Research* 27: 297–311 (1989).
Olney et al, "NMDA Antagonists as Neurotherapeutic Drugs, Psychotogen, Neurotoxins, and Research Tools for Studying Schizophrenia", Neuropsychopharmacology 1995—vol. 13, No. 4, pp. 335–345.

Primary Examiner—Nathan M. Nutter
Attorney, Agent, or Firm—Patrick D. Kelly

[57] ABSTRACT

Methods and compositions are disclosed for treating or preventing adverse CNS effects produced by NMDA receptor hypofunction (NRH), including hypofunction induced by NMDA antagonist drugs, and hypofunction occurring as a causative or aggravating factor in schizophrenia. One method of this invention comprises administering an alpha-2 adrenergic (α2) receptor agonist drug along with an NMDA antagonist drug. The NMDA antagonist drug exerts a primary benefit in reducing excitotoxic brain damage, alleviating neuropathic pain, or preventing or avoiding tolerance or addiction to various types of drugs. The α2 agonist drug acts as a secondary or "safener" drug, to prevent the neurotoxic side effects that would be caused by the NMDA antagonist in the absence of the safener drug. Another method disclosed herein involves the use of an α2 agonist drug, by itself, to combat a different and naturally-occurring form of NMDA receptor hypofunction which occurs as a causative or aggravating mechanism in people suffering from schizophrenia. Although α2 agonists are usually not effective in treating long-standing cases of chronic schizophrenia, where pathological changes in the brain have already reached or approached maximal levels, α2 agonists can be administered early in the illness, such as at the first signs of schizophrenic illness, and continuously or intermittently thereafter to prevent the development or worsening of pathological brain changes.

20 Claims, 2 Drawing Sheets

USE OF ALPHA-2 ADRENERGIC DRUGS TO PREVENT ADVERSE EFFECTS OF NMDA RECEPTOR HYPOFUNCTION (NRH)

GOVERNMENT SUPPORT

The research which led to this invention was supported in part by grants from the National Institutes of Health, including grants DA 06454, DA 05072, DA 07261, and AG 05681. Accordingly, the federal government has certain rights in this invention.

BACKGROUND OF THE INVENTION

The present invention relates to neurology and pharmacology, and to drugs for treating or preventing problems in the central nervous system (CNS). These problems involve abnormally low levels of activity at n-methyl-D-aspartate (NMDA) receptors; this condition is called, "NMDA receptor hypofunction" (NRH).

The following Background sections provide introductory information on NMDA receptors and several other types of receptors on the surfaces of neurons in the central nervous system, and on various neurotransmitters and drugs that either stimulate or suppress activity at these neuronal receptors.

Glutamate (GLU) and Neuronal Glutamate Receptors

Glutamate (sometimes abbreviated as GLU) is one of the 20 common amino acids used by all living cells to make protein. Glutamate is the ionized form of glutamic acid, which is its predominant form in neutral solutions, at pH 7.

In addition to its role as a building block in proteins, glutamate also plays an entirely distinct and crucial role in the central nervous system (CNS) of higher animals, including mammals and birds. Within the CNS, glutamate serves as the predominant excitatory neurotransmitter (e.g., Olney 1987; full citations to books and articles are provided below). In a brief overview, this process can be summarized as follows. At a neuronal synapse (i.e., a signal-transmitting junction between two nerve cells), a molecule of glutamate is released by the signal-transmitting neuron. The glutamate molecule enters the fluid in the gap between the two neurons, and it quickly contacts the exposed portion of a "glutamate receptor" on the surface of the signal-receiving neuron. This receptor is a protein molecule that straddles the cellular membrane of the signal-receiving neuron. Upon being activated (or "excited") by the glutamate molecule, the glutamate receptor molecule changes its conformation in a manner which briefly opens an ion channel which passes through the cell membrane. Calcium ($Ca^{++}$), sodium ($Na^+$), and certain other types of ions immediately flow through the ion channel, thereby altering a chemical ionic gradient that normally exists across the membrane of the neuron. This activates the neuron, causing it to release its own neurotransmitters.

To reset the mechanism and get the transmitting and receiving neurons ready to handle another nerve signal, the ion channel quickly closes, and the glutamate receptor releases the glutamate molecule. It floats back into the synaptic fluid between the neurons, where a molecular transport system intercepts it and pumps it back inside the transmitting neuron. The signal-receiving neuron restores its normal chemical gradients and regains a "polarized" condition ready to receive another nerve signal by pumping the calcium and sodium ions that had entered the cell, back out of the cell. This entire process occurs within a few milliseconds.

Since glutamate is an amino acid that can function as an excitatory neurotransmitter inside the CNS, it is often called an "excitatory amino acid" (EAA). Another type of amino acid, aspartate (the ionized form of aspartic acid), can also function as an excitatory amino acid in the CNS; therefore, glutamate receptors are sometimes referred to as EAA receptors, since they can be triggered by either glutamate or aspartate. However, glutamate is used much more widely than aspartate as a neurotransmitter, and EAA receptors (including both NMDA and non-NMDA receptors, discussed below) are referred to herein as glutamate or GLU receptors.

Types of GLU Receptors: NMDA and non-NMDA Receptors

This invention directly involves NMDA receptors, which are one class of glutamate receptors, and alpha-2 adrenergic receptors. To understand the full meaning of these terms, several terms need to be defined, and NMDA receptors must be contrasted with two other types of glutamate receptors.

A "receptor" as used herein refers to a macromolecular binding site which is at least partially exposed on the surface of a cell, and which has specific and limited affinity for one or more fluid-borne molecules called "ligands" (these usually are neurotransmitters or hormones). When a ligand contacts an appropriate receptor, a brief binding reaction occurs which triggers or otherwise evokes a cellular response, such as activation and depolarization of a neuron. Most receptor molecules are proteins which straddle the membrane of a cell, with an external portion for binding reactions and an internal portion which helps carry out the cellular response that occurs when the receptor is activated by a ligand.

This is not a rigid definition, and different scientists sometimes use the term "receptor" inconsistently; for example, they may either include or exclude various additional components, such as an ion channel which is opened or closed by a receptor. All of the glutamate receptors relevant to the present invention are associated with ion channels and therefore are referred to as ionotropic receptors.

In pharmacological terminology, an "agonist" is a molecule which activates a certain type of receptor. For example, glutamate molecules and drugs such as NMDA act as agonists when they excite EAA receptors. By contrast, an "antagonist" is a molecule which prevents or reduces the effects exerted by an agonist at a receptor.

There are three distinct types of ionotropic glutamate receptors in the mammalian central nervous system. Although all three receptor types are normally triggered by exactly the same EAA neurotransmitters in the CNS (i.e., glutamate or aspartate), these different subtypes of glutamate receptors have been found by researchers to have different binding properties when certain types of drugs are used as probes to study neuronal activity.

One major class of GLU receptors is referred to as NMDA receptors, since they bind preferentially to NMDA, which is n-methyl-D-aspartate. This analog of aspartic acid normally does not occur in nature, and is not present in the brain; it is, however, a useful probe drug which is widely used by neurologists. When molecules of NMDA contact neurons having NMDA receptors, they strongly activate the NMDA receptors and act as a glutamate agonist, causing the same type of neuronal excitation that glutamate causes.

The second class of glutamate receptors is called kainic acid (KA) receptors, since they are activated by kainic acid. The third class of GLU receptors is referred to herein as QUIS/AMPA receptors, since they are activated by both quisqualic acid (and its ionized form, quisqualate) and by alpha-amino-3-hydroxy-5-methyl-4-isoxazole (abbreviated as AMPA). Until the mid-to-late 1980's, AMPA receptors were called quisqualate (QUIS) receptors; however, quisqualate also activates a different type of receptor called a metabotropic receptor, so the recent trend is to call QUIS-type EAA receptors by the name "AMPA" receptors. KA receptors and QUIS/AMPA receptors are more closely related to each other (both structurally, and by higher levels of cross-affinity to certain drugs) than to NMDA receptors, and they are often referred to collectively as non-NMDA receptors.

The NMDA receptor complex (which includes an ion channel) has a number of distinct binding sites (also called recognition sites), where several different substances can bind to and modify the action of glutamate. Thus, there are several different types of NMDA antagonists, each type being defined in terms of the binding site with which it interacts.

Competitive NMDA antagonists compete with glutamate at the glutamate binding site (which is also the NMDA binding site). The action of glutamate at this site promotes opening of the ion channel to allow $Na^+$ and $Ca^{++}$ ions to flow into the cell. Competitive antagonists block the action of glutamate at this site, and prevent opening of the ion channel; thus, they are often referred to as "closed channel blockers."Competitive NMDA antagonists being developed by drug companies are usually given acronyms or code numbers, and they include, but are not limited to, compounds such as CPP (Boast 1988), D-CPP-ene (Herrling 1994), CGP 40116 (Fagg et al 1989), CGP 37849 (Fagg et al 1989), CGS 19755 (Boast 1988 and Grotta 1994), NPC 12626 (Ferkany et al 1989), and NPC 17742 (Ferkany et al 1993). Other competitive NMDA antagonists include D-AP5 (D-2-amino-5-phosphonopentanoic acid), D-AP7, CGP 39551 (D,L(E)-2-amino-4-methyl-5-phosphono-3-pentenoic acid carboxyethyl ester), CGP-43487, MDL-100, 452, LY-274614, LY233536, LY233053. Most of these agents have been shown to cause pathomorphological changes in the cerebral cortex of adult rats (Olney et al 1991; Hargreaves et al 1993), and all of them that have been tested in adult humans have been shown to cause psychotomimetic reactions such as hallucinations (Grotta 1994; Herrling 1994; Kristensen et al 1992).

There are also other sites in the NMDA receptor complex, located outside the ion channel, where glycine or certain types of polyamines can bind. Binding of glycine and polyamines to these sites exerts a cooperative action that assists glutamate in opening the ion channel. Agents that block the glycine or polyamine sites may have neuroprotective actions, comparable to competitive antagonists acting at the glutamate binding site, although only limited information is available concerning the neuroprotective potential of agents acting at the glycine or polyamine sites (Carter et al 1988). Glycine and polyamine site antagonists include but are not limited to kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetri- amine, 1,10-diaminodecane, 1,12-diaminododecane, ifenprodil, and SL-82.0715 (for reviews and citations, see Rogawski 1992 and Massieu et al 1993).

Within the NMDA receptor ion channel, there is a site where phencyclidine (PCP) and several other drugs (including dizocilpine, ketamine, tiletamine, and CNS 1102) bind selectively. When these agents bind to the PCP site in the ion channel, they block ion flow through the ion channel, even if the channel otherwise remains open: thus, drugs that block activity at NMDA receptors by binding to the PCP site are sometimes referred to as "open channel blockers".

Dizocilpine is the most selective and effective non-competitive NMDA antagonist ever discovered; it is powerful and highly selective at the PCP binding site. The full chemical name is (+)-5-methyl-10,11-dihydro-5H-di[a,d]-cyclohepten-5,10-imine. The maleate salt of dizocilpine is commercially available to researchers under the name MK-801, and MK-801 has been investigated extensively for use as an antiepileptic and for preventing damage due to cerebral ischemia. It has, however, been shown, even at relatively low doses, to produce pathomorphological changes in cerebrocortical neurons in adult rats (Olney et al 1989).

Phencyclidine is a dissociative anesthetic, formerly used in human and veterinary medicine, that is illicitly abused as a hallucinogenic drug under the street name "angel dust". This drug can induce a psychosis which is clinically indistinguishable from schizophrenia, and it has been shown at relatively low doses to produce pathomorphological changes in various corticolimbic regions of the adult rat brain (Olney et al 1989, Corso et al 1994).

Ketamine is a dissociative anesthetic that is currently being used in human anesthesia, and is the only NMDA antagonist that is currently being used for anesthetic purposes. It is suitable for human anesthesia because it has an exceedingly short duration of action (usually about 15 minutes), which assures that its effects on the CNS, including adverse CNS effects, can be rapidly reversed by termination of ketamine administration. Despite its short duration of action, it occasionally produces an "emergence" reaction during recovery from anesthesia that is characterized by unpleasant dreams, confusion, agitation, hallucinations, and irrational behavior. Ketamine has recently been studied for its psychotomimetic effects and has been described as an agent that produces symptoms in normal humans that are indistinguishable from the symptoms of psychosis and thought disorder seen in schizophrenia (Krystal et al 1994). Ketamine also has been shown to cause pathomorphological changes in the cerebral cortex of adult rats (Olney et al 1989).

Tiletamine, also used in veterinary medicine as an anesthetic, is another non-competitive NMDA antagonist which acts at the PCP binding site. It has also been shown to cause pathomorphological changes in the cerebral cortex of adult rats (Olney et al 1989).

Toxic Effects of Excessive NMDA Activity; Utility of NMDA Antagonists

Excessive activation of NMDA receptors by endogenous glutamate is thought to play a major role in a number of important CNS disorders. In an acute crisis such as a stroke or CNS trauma, and in certain other events such as severe epileptic seizures, the cellular transport mechanism that removes glutamate almost immediately from the synaptic fluid, and pumps it back inside a neuron for subsequent re-use, can run out of energy to drive the glutamate clearance process. If this occurs, excessive glutamate begins to accumulate in the synaptic fluid between neurons. If glutamate molecules are not being removed from synapses at adequate rates, they begin to repeatedly and persistently excite glutamate receptors on signal-receiving neurons. This drives the receptor-bearing neurons into a state of hyper-excitation which can kill the neurons, through a process called "excitotoxicity" (e.g., Olney 1990, Choi 1988, Choi 1992).

Excessive activity at NMDA receptors can also severely aggravate neuronal damage caused by trauma (mechanical injury) to the brain or spinal cord. Many trauma victims suffer from a dangerous and potentially lethal increase in intracranial pressure, which involves water flowing into neurons in an effort to sustain osmotic balance as charged ions flow into the neurons during neuronal excitation. Elevated intracranial pressure is a major cause of morbidity and mortality in CNS trauma victims, and NMDA antagonists are potentially useful in reducing intracranial pressures following such crises.

As used herein, the term "acute insult to the central nervous system" includes short-term events which involve or pose a threat of neuronal damage mediated by excitotoxicity or other forms of excessive stimulation of neurons by glutamate. This includes ischemic events (which involve inadequate blood flow, such as a stroke or cardiac arrest), hypoxic events (involving inadequate oxygen supply, such as drowning, suffocation, or carbon monoxide poisoning), trauma in the form of mechanical or similar injury, certain types of food poisoning which involve an excitotoxic poison such as domoic acid, and seizure-mediated neuronal degeneration, which includes several types of severe epileptic seizures. NMDA antagonists can help to protect neurons in the CNS against such damage (e.g., Olney 1990; Choi 1992), and a number of NMDA antagonists (i.e., drugs that can suppress excitatory activity at NMDA receptors) are actively under development by several major pharmaceutical companies.

In addition to neuronal damage caused by acute insults, excessive activation of glutamate receptors may also contribute to more gradual neurodegenerative processes leading to cell death in various chronic neurodegenerative diseases, including Alzheimer's disease, amyotrophic lateral sclerosis (Lou Gehrig's disease), AIDS dementia, Parkinson's disease and Huntington's chorea (Olney 1990). It is considered likely that NMDA antagonists will prove useful in the therapeutic management of such chronic diseases.

Excessive activation of NMDA receptors is also responsible for the generation of "neuropathic" pain, a type of pain which is sometimes called "neurogenic pain" or "wind-up" pain (Woolf et al 1989; Kristensen et al 1992; Yamamoto and Yaksh 1992). Neuropathic pain is a chronic condition in which NMDA receptors in neural pain pathways have become "kindled" to an abnormally high level of sensitivity so that they spontaneously convey nerve messages that the patient perceives as pain even though no painful stimulus has been inflicted. By mechanisms that are poorly understood, pathological changes associated with diabetes are conducive to the generation of neuropathic pain, a condition known as "diabetic neuropathy". One of the distinguishing characteristics of neuropathic pain is that morphine and related pain-killing drugs which are effective in controlling other types of pain are usually ineffective in controlling neuropathic pain (Backonja 1994). Several recent reports indicate that NMDA antagonists can prevent or ameliorate neuropathic pain (Davar et al 1991; Mao et al 1992; Seltzer et al 1991; Neugebauer et al 1993; Kristensen et al 1992; Backonja et al 1994).

NMDA receptor activation has also been implicated as a mechanism underlying the development of tolerance to various potentially addictive drugs. "Tolerance" is used broadly herein, to include any or all of the following: dosage-type tolerance to a drug, which implies that a person must take an increasing amount of a drug in order to achieve the same level of sensations or therapeutic benefit; dependence upon a drug, which implies that a patient must continue taking a drug to avoid withdrawal symptoms; and, craving for a drug, which can include physiological and/or psychological cravings. A number of recent reports indicate that in animal studies, NMDA antagonists apparently prevented the development of tolerance to opiate analgesics (Marek et al 1991; Trujillo and Akil 1991; Ben-Eliyahu et al 1992; Tal and Bennett 1993) or benzodiazepine anxiolytics (L. Turski et al, PCT patent application WO 94/01094). It has also been reported that ibogaine, a drug known to have NMDA antagonist properties, can suppress the craving for cocaine (e.g., Sershen 1994).

NMDA Receptor Hypofunction (NRH)

The term "NMDA receptor hypofunction" (NRH) is used herein to refer to abnormally low levels of activity at NMDA receptors on CNS neurons. As discussed in the immediately following paragraphs, NRH can occur as a drug-induced phenomenon, following administration of an NMDA antagonist drug such as PCP or MK-801. It can also occur as an endogenous disease process; the Applicants have discovered that NRH appears to be an important mechanism responsible for symptom formation and pathological brain changes in idiopathic psychotic disorders such as schizophrenia.

NRH as a Drug-Induced Phenomenon: Both Beneficial and Detrimental

As described above under the heading, "Utility of NMDA Antagonists", when NRH is induced by NMDA antagonists (i.e., drugs that block or otherwise suppress activity at NMDA receptors), it can have several important beneficial effects. However, despite these beneficial effects, NMDA antagonists can also create serious detrimental side effects. As described in Olney et al 1989b, and in U.S. Pat. No. 5,034,400 (Olney 1991), NMDA antagonists have been shown to damage or even kill neurons located in a portion of the brain known as the posterior cingulate or retrosplenial (PC/RS) cortex and in certain other cerebrocortical and limbic regions of the animal brain. NMDA antagonists can also cause hallucinations, transient psychoses, and other psychotomimetic side effects in adult humans (for reviews see McCarthy 1981, and Olney and Farber 1994). Thus, a major obstacle to the use of NMDA antagonists as neurotherapeutic drugs lies in their potential for inducing adverse CNS side effects, including brain damage and psychosis.

It has been discovered by the Applicants that several types of drugs can act as "safener" agents to reduce or prevent the adverse side effects that can be caused by NMDA antagonists. Safener drugs previously described by the Applicants include at least three different classes:

(1) anticholinergic drugs which block the muscarinic class of cholinergic receptors, such as scopolamine, atropine, benztropine, trihexyphenidyl, biperiden, procyclidine, benactyzine or diphenhydramine; see Olney et al 1991, and U.S. Pat. No. 5,034,400 (Olney 1991);

(2) certain types of barbiturates, such as secobarbitol, which are called "direct GABA agonists" (Olney et al 1991). Unlike benzodiazepine drugs such as diazepam (sold under the trademark VALIUM), which can only increase the effects of naturally occurring inhibitory neurotransmitter called gamma-amino-butyric acid (GABA), direct GABA agonists can activate GABA type A ($GABA_A$) receptors even in the absence of GABA.

(3) certain types of drugs that can bind to a class of receptors called sigma receptors (Farber et al 1993). These receptors are blocked by di(2-tolyl)guanidine and rimcazole, which are selective for sigma receptors, as well as other drugs such as haloperidol, thioridazine and loxapine, which interact with dopamine receptors as well as sigma receptors.

Despite the discoveries of those safening agents which can be used to reduce the toxic side effects of NMDA antagonists, there remains a need for improved treatments which take advantage of the beneficial effects of NMDA antagonists, while avoiding the adverse side effects that can be caused by NMDA antagonists. That type of improved treatment is one of the objects, and one of the disclosures, of this invention.

Based on several lines of evidence, discussed below, data gathered by the Applicants and by a number of other researchers indicate that the brain-damaging effects and the psychotogenic effects of NMDA antagonists apparently represent morphological and psychological manifestations of a single type of potentially toxic process, involving NMDA receptor hypofunction (NRH). It follows that any treatment effective in preventing the pathomorphological manifestations of drug-induced NRH in animals will also be effective in preventing at least some of the psychotic manifestations of drug-induced NRH in humans. In addition, as discussed below, any such treatment may have neurotherapeutic benefits in schizophrenia, in view of evidence identifying NRH as a mechanism that apparently causes or contributes to psychotic symptom formation and pathological brain changes in schizophrenia. Before these lines of evidence are presented in detail, another neuronal process needs to be analyzed, involving inhibitory neurotransmitter receptor systems and a potentially pathological process known as "disinhibition".

Inhibitory/Excitatory Transmitter Interactions; Disinhibition

It was mentioned above that in the CNS, glutamate is the principle type of excitatory neurotransmitter. Several other types of neurotransmitters also need to be discussed, since the interactions between glutamate and these systems are important to this invention.

Another major type of excitatory neurotransmitter molecule is acetyl choline (abbreviated as ACh). Like glutamate receptors, there are several different types of ACh receptors on neurons, which are divided into "muscarinic" and "nicotinic" classes of ACh receptors. The muscarinic class of ACh receptors is further subdivided into the m1, m2, m3, m4, and m5 subclasses. When a molecule of ACh contacts an ACh receptor on a neuron, this triggers a signal transduction process involving certain "second messenger" systems within the neuron, the net result being that a higher state of electrical activity is induced; this is another way of saying that the neuron is excited by ACh.

In the mammalian brain there also is a type of neurotransmitter receptor system referred to as the "sigma" receptor system. Although this system has been known for many years, progress has been slow in identifying the endogenous transmitter molecule that activates this system. However, recent evidence indicates that a certain peptide molecule that is abundantly contained in certain CNS neurons, called neuropeptide Y (NPY), has an important role in modulating the function of sigma receptors. The effects of NPY on the sigma receptor system are excitatory.

Therefore, in the brain circuitry that is relevant to the present invention, there are three excitatory transmitter receptor systems (glutamate, ACh, and sigma) and three excitatory transmitter molecules (glutamate, ACh and NPY).

In addition to the above three excitatory transmitter systems, there are also transmitter systems in the CNS that are primarily, or in some cases exclusively, inhibitory. The predominant inhibitory transmitter in the CNS is GABA (gamma-amino butyric acid). This inhibitory transmitter has important interactions with the glutamate excitatory system in many neural circuits within the CNS. Neurons that contain GABA and release GABA as an inhibitory transmitter are called GABAergic neurons.

In the particular neural circuitry relevant to the present invention (depicted in a simplified schematic manner in FIG. 1) glutamate is released in tiny amounts but on a continuous basis, by synapses that emerge from a neuron labelled as GLU neuron 10 in FIG. 1. Glutamate molecules being released by synapses which emerge from neuron 10 react with and activate NMDA receptors on the surfaces of three GABAergic neurons 20, 30, and 40 (as well another NMDA receptor on the surface of a norepinephrine (NE) neuron 50, as discussed below). This slow and steady release of GLU by neuron 10 provides a steady continuous driving force that keeps the GABAergic neurons 20, 30, and 40 in a constant state of activity, resulting in continuous release of GABA onto GABA inhibitory receptors on three different types of excitatory neurons, namely neurons that release glutamate (neuron 70), ACh (neuron 80), or NPY (neuron 60). Thus, glutamate, via its driving action on GABAergic inhibitory neurons, exerts "tonic inhibition" (the word "tonic" implies that it maintains a constant level of inhibitory tone) which restrains the activity of three separate excitatory pathways which use glutamate, ACh, and NPY as excitatory transmitters.

This represents an important principle (and an apparent paradox) of CNS activity, in which an excitatory neurotransmitter such as glutamate can cause suppression, rather than excitation, of neuronal activity. This is important not only for physiological functions in the CNS, but for understanding a mechanism called "disinhibition" which can contribute to dysfunction and degeneration of neurons in drug-induced or endogenous disease processes involving NMDA receptor hypofunction (NRH). Specifically, if the NMDA receptors which govern GABAergic neurons 20, 30, and 40 in FIG. 1 are blocked by an NMDA antagonist drug or rendered hypofunctional by a disease process, then the ability of neuron 10 to tonically inhibit the three excitatory neurons 60, 70, and 80 (via GABAergic neurons 20, 30, and 40) is lost. This loss of glutamate-mediated control is referred to herein as "disinhibition" of the inhibitory control mechanism that normally protects pyramidal neuron 90. When disinhibition occurs due to NMDA receptor hypofunction, all three excitatory neurons 60, 70, and 80 can begin to hyperstimulate and injure or kill PC/RS neuron 90.

All three of the excitatory neurons 60, 70, and 80 are coupled via axons to a pyramidal neuron 90, located in the posterior cingulate or retrosplenial (PC/RS) cortex of the brain. If all three of the excitatory neurons 60, 70, and 80 begin firing simultaneously, they can overstimulate pyramidal neuron 90 and begin pushing it to the point where it becomes so exhausted that it begins to suffer serious damage and eventually dies from overstimulation. The pyramidal neuron 90 is shown as having three different types of excitatory receptors: (1) kainic acid receptors, a type of non-NMDA glutamate receptor; (2) m3 receptors, a type of acetyl-choline muscarinic receptor; and, (3) sigma ($\sigma$) receptors, which are believed to be triggered by neuropeptide Y (NPY). The presence of all three types of excitatory receptors on pyramidal neurons is supported by the experimental evidence in Example 6.

The schematic depiction in FIG. 1 also depicts an inhibitory neuron 50, located in the brain stem, which normally secretes norepinephrine (NE) into the forebrain via long fibrous processes, upon being stimulated by glutamate. This additional regulatory mechanism is described in more detail below.

The highly simplified schematic depiction in FIG. 1 indicates that a single glutamate-releasing neuron 10 interacts with all four inhibitory neurons 20, 30, 40, and 50. This is shown merely to avoid excessive clutter in the drawing; in the extraordinarily complex circuitry of the brain of a higher animal, thousands and possibly millions of glutamate-releasing neurons will interact to sustain tonic inhibition of neuronal circuits involving thousands and possibly millions of inhibitory neurons. The important point is that many and perhaps most of these interactions are mediated by glutamate release and NMDA receptors, and the tonic inhibition circuitry can be suppressed and rendered incompetent by NMDA antagonist drugs, or by endogenous NRH in certain disease processes, as occur in schizophrenia.

Similarly, PC/RS neuron 90 merely represents one of thousands or millions of neurons which are at risk due to NMDA receptor hypofunction, and the neurons at risk are scattered widely throughout a number of different corticolimbic regions of the brain. The PC/RS cortical region is the focal point of the histological examinations described in the Examples because it is typically one of the most consistently and heavily damaged areas; however, this is not meant to imply that it is the only area damaged or at risk.

The circuit diagram in FIG. 1, which was developed on the basis of recent experiments by the Applicants, is not disclosed in the prior art, and is part of the Applicants' invention. It can help provide a frame of reference to understand numerous published reports describing the injury or death of neurons in cerebrocortical and limbic brain regions following treatment of rats with NMDA antagonist drugs, and it can also help explain the schizophrenia-like psychotic reactions observed in humans following treatment with NMDA antagonist drugs. In addition, as will be discussed in the following paragraphs, it can explain mental disturbances and pathological brain changes in idiopathic psychotic illnesses such as schizophrenia.

NRH as a disease mechanism

It has been known for years that phencyclidine (PCP), ketamine, and certain other related drugs which recently have been shown to block NMDA receptors by acting at a PCP binding site in the NMDA receptor complex, cause psychotic reactions in humans which closely resemble the symptoms displayed by schizophrenics (Luby et al 1962; McCarthy 1981; Krystal et al 1994). It has also been shown recently that various other drugs that inhibit NMDA receptor activity by binding to different sites within the NMDA receptor complex can also cause similar psychotic reactions in humans (Kristensen et al 1992; Herrling 1994; Grotta 1994). Accordingly, the ability of NMDA antagonists to induce psychosis correlates not with action just at the PCP receptor site, but with their ability to reduce NMDA receptor activity to abnormally low levels, regardless of site or mechanism of action causing the reduced NMDA receptor activity. Therefore, several authors have hypothesized that impairment of the NMDA receptor system may be a causative or aggravating factor in the formation of psychotic signs and symptoms in schizophrenia (e.g., Javitt and Zukin 1991).

As used by most clinicians, the term "signs" refers to external manifestations that can be objectively assessed by a trained clinician, while "symptoms" generally refers to subjective complaints or comments made by a patient.

In recent years, there has been a tendency to subdivide the symptoms of schizophrenia into at least two categories, referred to as negative symptoms (e.g., levels of emotional withdrawal, blunted affect, autism, avolition, or anhedonia which extend beyond the normal ranges displayed by competent adults), and positive symptoms (e.g., hallucinations, which includes auditory and tactile as well as visual hallucinations, and delusions). Clinicians trained in the schizophrenia field have commented repeatedly that the mental disturbances induced by these NMDA antagonist drugs faithfully mimic both the negative and positive symptoms of schizophrenia (e.g., Javitt and Zukin 1991; Krystal et al 1994).

It has also been increasingly recognized in recent years that the brains of schizophrenic patients show evidence of pathomorphological changes in corticolimbic regions (Bogerts 1993), just as the brains of rats treated with NMDA antagonist drugs show evidence of pathomorphological changes in corticolimbic regions (Olney et al 1989; Corso et al 1994). These correlations have strengthened the belief that NRH, the mechanism by which NMDA antagonist drugs cause both psychotic and pathological brain changes, is the same mechanism causing these two types of changes in schizophrenia. It follows that any treatment that effectively prevents corticolimbic brain damage associated with the NMDA receptor hypofunction induced by NMDA antagonist drugs, is a promising treatment which, in at least some patients, will be able to prevent or ameliorate some or all of the psychotic symptoms (both positive and negative) and structural brain changes in schizophrenia.

Additional background information on the correlations between NMDA antagonists and schizophrenia is discussed in more detail in Olney and Farber 1995.

In the list of References, which begins on page 48, please modify the Olney and Farber 1995 ("in press") citation to read as follows:

Olney, J. W. and Farber, N. B., "NMDA antagonists as neurotherapeutic drugs, psychotogens, neurotoxins, and research tools for studying schizophrenia," *Neuropsychopharmacology* 13: 335–345 (1995)

The Adrenergic Transmitter System

This section provides background information on what was known about the alpha-2 adrenergic (α2) system prior to this invention. The involvement of this receptor system in reducing or preventing the toxic side effects of NMDA receptor hypofunction is part of the subject invention. Although a number of prior research reports indicate that NMDA receptor activity is linked somehow to various other receptors and neurotransmitters, none of the prior art suggested any involvement of α2 receptors in the neurotoxic side effects that can be caused by NMDA antagonists, or in the adverse CNS effects associated with NMDA receptor hypofunction.

An overview of the adrenergic neurotransmitter and receptor system is provided by Dahlstrom (pp. 11–14) and Dickinson and Lefkowitz (pp. 14–16) in Adelman's *Encyclopedia of Neuroscience* (1987). For more detailed reviews, see Ruffolo et al 1993 or Louis et al 1988. Briefly, norepinephrine (also called noradrenalin) is a neurotransmitter that is synthesized and secreted primarily by certain large neurons clustered in the brain stem. These neurons send long axonal processes to many regions of the forebrain, including the cerebral cortex, where they contact various forebrain neurons. Acting through these long axonal processes, the neurons which originate in the brain stem release norepinephrine into the forebrain. The effects of norepinephrine in the CNS are usually inhibitory and are often mediated by a mechanism involving inhibition of the release of other transmitters from neurons in the forebrain. In addition, some α2 receptors apparently have an auto-regulating function; when activated by norepinephrine, they apparently act to suppress the release of additional norepinephrine by neurons (Trendelenburg et al 1993).

Neuronal receptors which are triggered by norepinephrine or epinephrine (also called adrenalin) are called adrenergic receptors. These adrenergic receptors are divided into two classes, alpha and beta, which are subdivided into α1, α2, β1, and β2 classes. The α2 class is further subdivided into several subclasses, but no consensus nomenclature has yet emerged for these subclasses (see Ruffolo et al 1993). Norepinephrine is strongly active at all α1 and α2 adrenergic receptors, and has weak activity at β receptors. Epinephrine has roughly equal activity at both α and β adrenergic receptors.

Alpha-2 adrenergic receptors within the central nervous system are of interest herein; for convenience, these are referred to hereafter simply as α2 receptors. As noted above, norepinephrine (the natural neurotransmitter) activates both α1 and α2 adrenergic receptors. By contrast, several selective α2 agonist drugs (including clonidine, iodoclonidine, guanabenz, guanfacine, xylazine, lofexidine, medetomidine, dexmedetomidine, tizanidine, rilmenidine, azepexole, alpha-methyldopa, and alpha-methylnoradrenaline) have been discovered which activate α2 receptors with higher affinity than they have for α1 receptors. Most of these drugs which are of commercial interest are used clinically as anti-hypertensive drugs, to help reduce blood pressure in patients suffering from hypertension. Several have been used in human anesthesia, either alone or in combination with various opiates or inhalational anesthetics such as halothane (e.g., Doze et al 1989; Goodman and Gilman 1990, p. 308) and have been found to reduce the dose requirement for opiates or inhalational anesthetics. It has also been reported on the basis of animal studies that α2 agonist drugs can by themselves partially alleviate neuropathic pain (e.g., Puke and Wiesenfeld-Hallin 1993; Zeigler et al 1992; Danzebrink and Gebhart 1990).

Some α2 agonists have also been used in veterinary anesthesia. In veterinary medicine, a combination of ketamine (a dissociative anesthetic which has recently been shown to be an NMDA antagonist) with an α2 agonist such as xylazine or medetomidine has been administered to improve the duration and quality of anesthesia for animals and to reduce the dose requirement for ketamine (Verstegen 1989; Nevalainen et al 1989; Moens and Fargetton 1990).

At least two α2 agonists, clonidine and lofexidine, have also been tested by researchers to evaluate their ability to help reduce withdrawal symptoms in people addicted to cigarettes or opiates (e.g., Siegel et al 1985; Segal 1985; Green and Cordes 1989). Lofexidine is currently considered the agent of choice in Great Britain for attenuating opiate withdrawal symptoms, because of its reduced hypotensive side effects compared to clonidine (Washton et al 1983). While these drugs reportedly help reduce withdrawal symptoms in some recovering addicts, they are not generally considered effective in preventing the development of tolerance and physical dependence.

Clonidine has also been tested to see whether it can treat schizophrenia. As described in more detail below, the results were not satisfactory, and it is not in clinical use today as a treatment for schizophrenia.

None of these references disclose the use of an α2 agonist to block the neurotoxic side effects of an NMDA antagonist, nor do they suggest use of a combination of an α2 agonist with an NMDA antagonist which (unlike ketamine) has a sufficiently long duration of action to be of value for use as described herein. In addition, it was not heretofore recognized that the α2 receptor system has an inhibitory effect on neurons involved in the neurotoxic side effects caused by NMDA antagonists and by NMDA receptor hypofunction.

Accordingly, one object of the present invention is to disclose a method of using NMDA antagonist drugs in combination with α2 agonist drugs to reduce neuronal damage caused by acute insults to the CNS. By using an NMDA antagonist, excitotoxic and possibly other damage relating to excessive NMDA receptor stimulation can be reduced or prevented. By co-administering an α2 agonist drug with the NMDA antagonist, the neurotoxic side effects of the NMDA antagonist, such as hallucinations and damage to PC/RS cortical neurons, can be reduced or prevented.

Another object of this invention is to disclose a method of using NMDA antagonists in conjunction with α2 agonists for controlling neuropathic pain.

Another object of this invention is to disclose a method of using NMDA antagonists in conjunction with α2 agonists for preventing the development of tolerance to, dependence on, and craving for opiates and certain other drugs.

Another object of this invention is to disclose a method of using α2 agonist drugs to treat the clinical signs and symptoms of schizophrenia, and to prevent the pathological brain changes that accompany and aggravate schizophrenia.

These and other objects of this invention will be clarified and explained in the following summary and detailed description.

SUMMARY OF THE INVENTION

The present invention relates to novel methods and compositions for treating or preventing adverse CNS effects produced by NMDA receptor hypofunction (NRH), including hypofunction induced by NMDA antagonist drugs, and hypofunction occurring as a causative or aggravating factor in idiopathic psychotic disease processes such as schizophrenia.

One method of this invention comprises administering an alpha-2 adrenergic (α2) receptor agonist along with an NMDA antagonist drug to reduce excitotoxic brain damage during or after an acute CNS insult such as a stroke, cardiac arrest, or CNS trauma, or to reduce excitotoxic brain damage caused by a chronic neurodegenerative disease. The NMDA antagonist exerts a primary effect in reducing glutamate-mediated excitotoxicity, while the α2 agonist drug acts as a secondary or "safener" drug, to prevent the neurotoxic side effects that would be caused by the NMDA antagonist in the absence of the safener drug.

Another method disclosed herein involves the use of an NMDA antagonist for alleviating neuropathic pain, or for preventing or reducing the development of tolerance or addiction to various types of addictive drugs. As above, an α2 agonist drug is co-administered as a safener drug with the NMDA antagonist, to prevent the adverse side effects that could be caused by the NMDA antagonist in the absence of the safener drug.

Since all of the conditions anticipated in this invention for which an NMDA antagonist would be used require relatively long-term treatments, NMDA antagonists having a substantially longer duration of action than ketamine would be preferred or required. For example, various NMDA antagonists such as MK-801 have a duration of action measured in days, compared to ketamine's action as a rapidly reversible anesthetic with an action lasting roughly 15 minutes.

Yet another method disclosed herein involves the use of an α2 agonist drug, by itself, to combat a different and naturally-occurring form of NMDA receptor hypofunction, which occurs as a causative or aggravating mechanism in people suffering from schizophrenia. Although α2 agonists are usually not effective in treating long-standing cases of chronic schizophrenia, where pathological changes in the brain have already reached or approached maximal levels, α2 agonists can be administered early in the illness, such as at the first signs of schizophrenic illness, and continuously thereafter to prevent the development or worsening of psychosis and pathological brain changes.

DESCRIPTION OF THE PREFERRED EMBODIMENTS

In the present invention it has been discovered that α2 receptors are critically involved in the neuronal circuitry which mediates certain adverse CNS effects caused by NMDA receptor hypofunction (NRH). Accordingly, this invention discloses a method for treating (this term is used broadly, to include preventive as well as therapeutic treatment) adverse CNS effects produced by NRH. This method comprises administering, to a human or other mammalian patient, an alpha-2 adrenergic (α2) agonist drug (which includes pharmacologically acceptable salts of such drugs), in an amount effective for inhibiting the adverse CNS effects produced by NRH.

In one embodiment of this method, it has been discovered that drugs which activate α2 receptors (such as clonidine, iodoclonidine, guanabenz, guanfacine, xylazine, lofexidine, medetomidine, dexmedetomidine, tizanidine, rilmenidine, azepexole, alpha-methyldopa, and alpha-methylnoradrenaline) can be co-administered with NMDA antagonists to reduce the toxic side effects of NMDA antagonists without blocking the beneficial primary effects of NMDA antagonists. This allows the use of such α2/NMDA drug combinations for a number of valuable therapeutic purposes, including: (1) prevention of neuronal degeneration associated with acute CNS injury syndromes, including hypoxia/ischemia (stroke), cardiac arrest, asphyxia, CNS trauma, and major epileptic seizures; (2) prevention of gradual excitotoxic neuronal degeneration which may accompany various progressive degenerative diseases, such as Alzheimer's disease, amyotrophic lateral sclerosis, AIDS dementia, Parkinson's disease, and Huntington's chorea; (3) alleviation of chronic neuropathic pain, and, (4) prevention of tolerance or addictive responses to certain types of potentially addictive drugs, including opiates, sedatives, anxiolytics, and possibly cocaine.

In another embodiment of this invention, α2 agonist drugs can be administered by themselves, on a preventive basis, to protect against pathological brain changes mediated by NRH that occurs as a disease mechanism in idiopathic psychotic illnesses such as schizophrenia.

In the following paragraphs, these several uses are discussed in more detail under separate headings.

Figure 1:
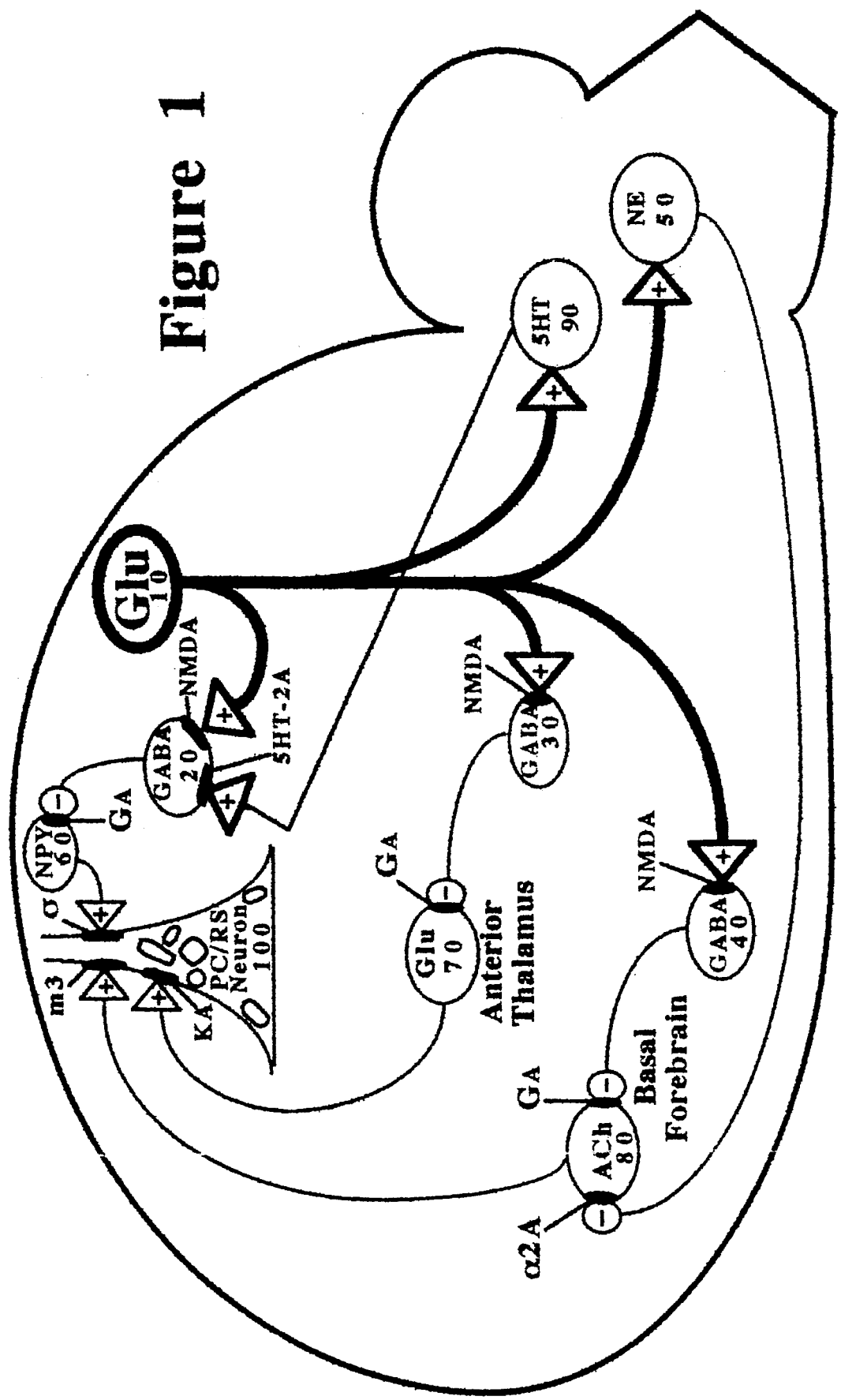
FIG. 1 is a schematic depiction of a neural circuit in the brain. In this circuit, a glutamate-releasing neuron stimulates other neurons that release inhibitory neurotransmitters. These inhibitory neurotransmitters act at other neurons in a manner that protects a pyramidal neuron in the posterior cingulate or retrosplenial (PC/RS) cortex against toxic overstimulation.

A schematic depiction of a neuronal circuit arrangement, which can be used to help understand the neuronal mechanisms involved in this invention, is provided as part of FIG. 1. In that figure, neurons which are located in the brain stem and which secrete norepinephrine (NE) into synaptic junctions in the forebrain and elsewhere via long fibrous processes are schematically depicted by NE neuron 50. Under normal and healthy conditions, NE neuron 50 is kept in a state of continuous activity, as described in the Background section, by slow and steady release of glutamate from one or more GLU neurons 10. The glutamate neuron 10 activates the NE neuron 50 via an NMDA receptor on the NE neuron 50. In response to this activation, the NE neuron 50 releases a slow and steady supply of norepinephrine, which can act as an inhibitor at any of several possible synaptic locations, including an α2 receptor on the main body of acetyl choline neuron 80. Release of tonically inhibitory quantities of NE into this synapse would help protect the pyramidal neuron 90 against overexcitation.

By this mechanism, suppression of activity at the NMDA receptor on neuron 50, either by drugs such as NMDA antagonists or as part of a disease process involved in schizophrenia, will reduce or block the ability of neuron 50 to help protect pyramidal neuron 90. However, this NRH-induced problem can be overcome by administering an α2 agonist drug which can stimulate the α2 receptor on ACh neuron 80. The α2 agonist drug provides a pharmaceutical means for bypassing the silenced NE neuron 50 and suppressing ACh release from ACh neuron 80, thereby protecting the pyramidal neuron 90 from overstimulation.

Although most α2 agonists have some degree of affinity for both α1 and α2 adrenergic receptors, several (including dexmedetomidine and possibly azepexole; see Doze et al 1989, and Goodman and Gilman 1990 at page 308) have been identified which appear to have substantially more selectivity for α2 receptors than for α1 receptors, when compared to clonidine (clonidine is the most widely used α2 agonist, and it is generally regarded as the standard α2 agonist for most comparative purposes). In addition, as mentioned above, at least one α2 agonist (lofexidine) has been identified which has substantially lower hypotensive side effects than clonidine (Washton et al 1983). In general, it is often assumed that highly selective neuroactive drugs which act only at a particular target receptor are likely to have fewer and milder side effects than other agents which are less specific and have higher levels of affinity for more than one type of receptor. Accordingly, α2 agonists which have (1) higher selectivity for α2 receptors than clonidine, and/or (2) lower hypotensive effects than clonidine, are generally preferred as candidates for evaluation for use as described herein, for the reason that they are likely to cause fewer and/or milder unwanted side effects.

As used herein, the phrase "α2 agonist" refers to a drug which has a substantial activating effect at α2 adrenergic receptors in the CNS, including drugs such as clonidine which also have substantial activity at α1 receptors. The phrase "highly selective α2 agonist" refers to an α2 adrenergic agonist (such as dexmedetomidine) which has substantially higher selectivity for α2 receptors (and substantially lower affinity for α1 receptors) than clonidine. Reports indicated that such drugs include guanfacine, dexmedetomidine, and azepexole, and this class of highly selective α2 agonists may include lofexidine and various other α2 agonists as well. The phrase "α2 agonist which has little hypotensive side effect" refers to an α2 agonist which has substantially lower activity in reducing blood pressure than clonidine; reports indicate that this includes lofexidine and guanfacine, and various other α2 agonists may also qualify.

Although the Applicants are not aware of any publication that systematically ranks or quantifies numerous α2 agonists in terms of α2 selectivity, severity or absence of side effects, and ability to penetrate mammalian blood-brain barriers, such information is provided in various locations (e.g., Goodman and Gilman 1990 at page 308; Ruffolo et al 1993 at page 264; Doze et al 1989 at page 75). In addition, evaluation for these relevant properties on any known or hereafter-discovered α2 agonist can be carried out with routine experimentation using conventional procedures. Such tests include competitive binding assays to evaluate selectivity for α1 and α2 receptors; tests on both normal and hypertensive lab animals to evaluate hypotensive activity; and analysis of CNS tissue following administration of radiolabelled drugs, to evaluate BBB permeability. Accordingly, based on the teachings herein, methods are provided for screening the α2 agonist drugs listed herein, or any other α2 agonist drugs which are currently known or hereafter discovered, and determining which ones have the combination of traits that are preferred for use as described herein, comprising (1) high selectivity for α2 receptors, (2) low hypotensive effects, and (3) high levels of permeability through mammalian blood-brain barriers.

Use of α2 Agonists and NMDA Antagonists to Treat Excitotoxicity

The Applicants have found that administration of an α2 agonist together with an NMDA antagonist can prevent the NMDA antagonist from causing neurotoxic side effects without interfering with the NMDA antagonist's primary beneficial effect in preventing or reducing neuronal death caused by excitotoxic events. These tests, which used adult mammalian lab animals, are described in more detail in Example 1. Briefly, rats were injected with MK-801, a powerful, highly selective, and relatively long-lasting NMDA antagonist. Each test rat also received an α2 agonist drug (clonidine, guanabenz, xylazine, or p-iodoclonidine), while control rats received an inert carrier. After 4 hours, the rats were sacrificed, and brain tissue from specific regions which are susceptible to NRH damage (layers III and IV of the posterior cingulate (PC) and retrosplenial (RS) cortices) were examined for vacuoles in the neurons, which are an indicator of neurotoxicity induced by NMDA receptor hypofunction. The results, in Table 1, indicated that the α2 agonist drugs were effective in preventing the vacuoles.

In a related series of tests, described in Example 3, it was shown that α2 agonists do not interfere with the useful beneficial effects of MK-801.

In the use of NMDA antagonists for any of the beneficial purposes described herein, it will be preferred and in many cases necessary to use NMDA antagonists which have a longer duration of action than ketamine. As noted in the Background section, ketamine is sometimes well-suited for human anesthesia because it has an exceedingly short duration of action (usually about 15 minutes); this assures that its effects on the CNS, including potentially adverse CNS effects, can be rapidly reversed by simply terminating ketamine administration. By contrast, in most cases which involve preventing excitotoxic damage, controlling neuropathic pain, or avoiding the development of tolerance to addictive drugs, other types of NMDA antagonists will need to be used which have substantially longer durations of actions, such as several hours or days.

Treatment of Neuropathic Pain

In view of evidence that NMDA antagonists may be effective in alleviating neuropathic pain (e.g., Davar et al 1991) and that α2 agonists, although not very effective, are the only other agents that can even partially alleviate neuropathic pain (e.g., Puke and Wiesenfeld-Hallin 1993; Zeigler et al 1992; Danzebrink and Gebhart 1990), it is anticipated that when an α2 agonist is co-administered with an NMDA antagonist to treat neuropathic pain, the two drugs together will have a powerful effect in alleviating the neuropathic pain, while avoiding the adverse side effects that would be caused by the NMDA antagonist in the absence of the α2 agonist. As mentioned in the Background section, opiates such as morphine are not effective in alleviating neuropathic pain; this is one of the distinguishing characteristics which define certain types of pain as "neuropathic" pain. As noted above, α2 agonist drugs are substantially less effective than NMDA antagonists in alleviating neuropathic pain, and there are no other currently satisfactory methods of alleviating neuropathic pain. Accordingly, combined treatment using both α2 agonists and NMDA antagonists will meet an important need in the clinical management of this type of pain.

Avoidance of Tolerance and Addiction

In most cases of chronic pain other than neuropathic pain, opiate analgesics are initially very effective in alleviating the pain, but the patient rapidly develops tolerance to the opiate so that an escalation of the opiate dosage is required to keep the pain under control. This can lead to physical dependence on and addiction to the opiate.

In a new type of chronic pain treatment disclosed herein, three different drugs are used. A relatively low dosage of an opiate analgesic is administered, to treat the chronic pain. An NMDA antagonist is also administered, to prevent or reduce the development of tolerance or addiction to the opiate analgesic. As the third component, an α2 agonist drug is also administered, to prevent any neurotoxic side effects from being caused by the NMDA antagonist. Accordingly, this invention discloses a mixture comprising an opiate analgesic, an NMDA antagonist to reduce the development of tolerance or addiction to the opiate analgesic, and an α2 agonist drug to prevent any neurotoxic side effects from being caused by the NMDA antagonist.

Treatment of Schizophrenia

When NMDA receptor hypofunction (NRH) is induced in the brain by an NMDA antagonist drug, the disinhibition process results in psychosis in humans and neuropathological changes in corticolimbic brain regions in the rat. These neuropathological changes cause permanent deficits in cognitive function (Brosnan-Watters et al 1994). Psychosis, neuropathological changes in corticolimbic brain regions, and cognitive deterioration, are all hallmark characteristics of schizophrenia (reviewed in Olney and Farber 1995).

Because of the numerous similarities and correlations between the mental aberrations (both positive and negative types, as discussed in the Background section) and pathological brain changes caused by NMDA antagonist drugs, and the mental aberrations and pathological brain changes observed in schizophrenia, and additionally in view of the Applicants' research described herein which has further elucidated several aspects of the neural circuitry underlying these aberrations and pathological changes, NMDA receptor hypofunction apparently is an important component of the cellular disruptions and disturbances in neural circuitry that characteristically occur in schizophrenia. Regardless of whether NRH is the sole causative mechanism responsible for all signs and symptoms of schizophrenia, or is responsible for only some manifestations of the disease, the findings described herein indicate that drugs which prevent pathological brain changes induced by NRH in experimental animals can be used for the therapeutic management of schizophrenia and, if applied properly, can prevent or ameliorate at least some signs and symptoms of the disease.

Accordingly, this invention discloses a method for treating schizophrenia, comprising the administration of an α2 agonist drug in a timely manner, beginning immediately or as soon as practical after the onset of symptoms, in order to prevent the NRH mechanism from causing pathological brain changes that can render subsequent treatment less effective or entirely ineffective. It is anticipated that in many and perhaps most patients, long-term maintenance-type treatment using oral or slow-release formulations will be preferred on a precautionary basis, to avoid the mental aberrations and pathological brain changes that would occur in the absence of long term maintenance therapy. In other patients, intermittent or episodic treatment may be preferred, such as during periods of stress at work or home.

It has long been known that excessive quantities of norepinephrine (NE) are often found in the brain tissue and cerebrospinal fluid of schizophrenics; for a review article, see Tassin 1992. Despite the surplus of NE in the brains of many schizophrenics, several researchers have tested NE agonists (including clonidine) on schizophrenia, even though such agonists, which act like norepinephrine, would normally be expected to aggravate, rather than reduce, any problems caused by already-high levels of norepinephrine. Apparently, one of the hopes of such research was that an agonist which is selective for a particular subtype of NE receptor might help reduce the expression of additional NE, due to the putative autoregulatory mechanism described earlier in which NE stimulation of NE receptors tends to suppress additional secretion of more NE.

Accordingly, several researchers tested clonidine, an alpha-2 adrenergic agonist, on patients with schizophrenia. The results were inconclusive at best, and are generally regarded as negative. In "open trial" studies, in which blinded control procedures were not employed, one report indicated a favorable response to clonidine (Lechin et al 1980), but three other published reports indicated that chronic schizophrenic patients failed to respond to clonidine (Simpson et al 1967; Sugerman 1967; Jimerson et al 1980). In more recent studies with double-blinded controls, the results were also negative, inconsistent, or inconclusive; Freedman et al 1982 reported that clonidine had some useful results in eight chronic schizophrenic patients, and van Kammen et al 1989 reported that four out of thirteen schizophrenic patients showed some improvement with clonidine treatment, but Ko et al 1983 observed no antipsychotic responses in a group of hospitalized chronic schizophrenics.

Because of the inconsistent and generally negative results of these studies, clonidine has not been used as an antipsychotic drug for the treatment of schizophrenia, except in experimental trials as just described. It is not used clinically to treat schizophrenia, and it is not generally believed by those knowledgeable in this field that alpha-2 adrenergic agonists are effective in ameliorating the symptoms of schizophrenia.

In contrast to the results of experimental tests on patients who were suffering chronically from severe signs and symptoms of schizophrenia, this invention discloses that $\alpha 2$ agonist drugs can help prevent and avoid the brain damage associated with schizophrenia, by administering an $\alpha 2$ agonist on a prophylactic basis, beginning as soon as possible after the first signs and symptoms of schizophrenic psychosis, before the NRH mechanism can induce pathological brain changes. By administering an $\alpha 2$ agonist immediately at the onset of symptoms and continuously thereafter on a chronic basis, or in anticipation of a period of unusual stress in a patient's workplace or home or family life, the $\alpha 2$ agonist can prevent or reduce the pathological brain changes and cognitive deterioration that would otherwise occur over the long term. None of the published studies pertaining to the effects of clonidine in well-established long-term schizophrenia patients carried out this form of treatment. The patients treated with clonidine in these studies were chronically ill and had been subject to the disease process for a long time; most had been hospitalized for years, and in a number of cases, the fact that their schizophrenia was refractory to other, more conventional treatments was a criterion for including them as candidates for experimental clonidine therapy. Therefore, the treatment disclosed herein is new and distinct from any of the experimental studies that have been carried out previously using clonidine.

Modes of Administration

The methods and compositions of this invention comprise either (1) an alpha-2 adrenergic ($\alpha 2$) agonist to be administered on its own, to protect against damage caused by naturally-occurring NMDA receptor hypofunction (NRH) as occurs in schizophrenia; or, (2) an $\alpha 2$ agonist in combination with an NMDA receptor antagonist, to protect against the toxic side effects of the NMDA antagonist, which is being used for a therapeutic purpose such as reducing excitotoxic brain damage in a stroke patient, or treating neuropathic pain.

The preferred dosage and mode of administration of an $\alpha 2$ agonist for preventing NRH-related neuronal damage will depend upon a number of factors. For example, if an $\alpha 2$ agonist is coadministered as a "safening" agent along with an NMDA antagonist that is being used to prevent excitotoxic brain damage, then the relevant factors will include (1) the potency and dosage of the NMDA antagonist being used; (2) the abilities of the NMDA antagonist and the $\alpha 2$ agonist to penetrate the blood-brain barrier; (3) the severity of the neurotoxic side effects produced by that NMDA antagonist in the absence of a safening agent; and, (4) whether the $\alpha 2$ agonist is being administered before, after, or simultaneously with the NMDA antagonist. The quantity of an $\alpha 2$ agonist which should be co-administered with an NMDA antagonist is that dosage required to prevent or minimize the appearance of neurotoxic manifestations when that NMDA antagonist is used. Such neurotoxic manifestations, and the dosage of a candidate $\alpha 2$ agonist which can avoid such toxic manifestations, can be determined by tests on rodents or primates which search for cellular manifestations in the brain, such as vacuole formation, mitochondrial damage, heat shock protein expression, or other pathomorphological changes in neurons of the cingulate and retrosplenial cerebral cortices. These cellular changes can also be correlated with abnormal behavior in lab animals. In human patients, since direct examination of brain tissue is not feasible, the appearance of hallucinations or other psychotomimetic symptoms, such as severe disorientation or incoherence, should be regarded as signals indicating that potentially neurotoxic damage is being generated in the CNS by an NMDA antagonist. Additionally, various types of imaging techniques, such as CAT scans, MRI imaging, and techniques that used labelled substrates to identify areas of maximal activity in the brain, may also be useful for determining preferred dosages of $\alpha 2$ agonists for use as described herein, with or without NMDA antagonists.

The terms, "drug", "agonist", and "antagonist," as used herein, includes so-called "pro-drugs" which are administered in a form that is known and intended to be metabolized, inside a patient's body, into a different form which has a specific desired activity. As an example, $\alpha$-methyldopa is a pro-drug form of an $\alpha 2$ agonist; the dopa form is actively transported into the CNS, which is desirable, and then enzymes inside the CNS convert the dopa form into $\alpha$-methyl-norepinephrine, which is the active α2 agonist form of the drug. In such cases, both α-methyldopa and α-methyl-norepinephrine would be regarded as α2 agonist drugs for the purposes of this invention.

The compositions of this invention may be administered by any suitable route which will introduce the intended drug(s) into the bloodstream. Depending on the specific NMDA antagonist and/or α2 agonist being used, the main candidate routes of administration will generally include oral ingestion of tablets, capsules, or liquids; intramuscular, or intravenous injection; subcutaneous implantation of slow-release devices or formulations or osmotic mini-pumps; transmembrane routes, such as lozenges, sublingual tablets or wafers, chewing gum, intranasal sprays, skin patches, or permeating lotions or ointments; and rectal suppositories, such as for non-physician administration to patients who cannot be relied upon to take their medicine. Such preparations are all well known in the pharmaceutical arts, and comprise as active ingredients an alpha-2 adrenergic agonist, or an alpha-2 adrenergic agonist in combination with an NMDA antagonist, and a pharmaceutically acceptable carrier. In making the compositions, the active ingredient or ingredients will usually be mixed with and diluted by a carrier, or enclosed within a carrier such as a capsule. When the carrier serves as a diluent, it may be a solid, semisolid or liquid material which acts as a vehicle, excipient or medium for the active ingredient. Thus the composition can be in the form of tablets, pills, powders, lozenges, chewing gum, cachets, elixirs, emulsions, solutions, syrups, suspensions, aerosols (as a solid or in a liquid medium), ointments containing for example up to ten percent by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

For oral administration, the compositions of this invention can be admixed with carriers and diluents molded or pressed into tablets or enclosed in gelatin capsules. Alternatively, the mixtures can be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

The compositions are preferably formulated or packaged in a unit dosage form, each dosage unit containing an effective amount of one or more alpha-2 adrenergic receptor agonists. The term "unit dosage form" refers to physically discrete units (such as capsules, tablets, or loaded syringe cylinders) suitable as unitary dosages for human subjects and other mammals, each unit containing a predetermined quantity of active material or materials calculated to produce the desired therapeutic effect, in association with the required pharmaceutical carrier. The amount of alpha-2 adrenergic receptor agonist preferred for a unit dosage will depend upon the amount and potency of the NMDA antagonist being administered (if any), or upon the severity of the psychotic onset symptoms being observed in a schizophrenic or other patient, and upon the efficacy of the given alpha-2 adrenergic agonist. Except when responding to acute events such as stroke, cardiac arrest, or drowning, when higher dosages may be required, the preferred dosage of an α2 agonist will usually lie within the range of from about 0.001 to about 1000 mg, more usually from about 0.01 to about 500 mg per day. The amount of the NMDA antagonist will also depend upon the efficacy of the NMDA antagonist but will typically be within the range of from about 0.001 to about 1000 mg, more usually from about 0.01 to about 500 mg per day.

The compositions of the present invention are effective over a dosage range that is dependent upon the particular compound used and the effects being treated or prevented. For example, the compositions containing an effective dose of an alpha-2 adrenergic receptor agonist will normally comprise dosages that fall within the range of about 0.00002 to about 50 mg/kg of body weight. When the preparation contains an NMDA antagonist, the NMDA antagonist will be present in an amount to give a dose range of from about 0.00002 to about 50 mg/kg of body weight. In treating adult humans, the composition preferably contains an α2 agonist in an amount within the range of about 0.0002 to about 20 mg/kg body weight. When an NMDA antagonist is also present in the composition, the effective amount of the NMDA antagonist will normally fall within the range of about 0.0002 to about 20 mg/kg body weight. However, it will be understood that the amount of the compound actually administered will be determined by a physician, in the light of the relevant circumstances including the condition or conditions to be treated, the choice of composition to be administered including the particular alpha-2 adrenergic agonist or the particular NMDA antagonist, the age, weight, and response of the individual patient, the severity of the patient's symptoms, and the chosen route of administration. Therefore, the above dosage ranges are intended to provide general guidance and support for the teachings herein, but are not intended to limit the scope of the invention.

Industrial Utility

The methods of this invention are useful in facilitating the safe treatment and prevention of pathological processes associated with NMDA receptor hypofunction, and in the actual treatment and prevention of these pathological processes. Notably, this invention diminishes the side effects produced by either (1) NMDA antagonist drugs, which can be useful in situations involving a risk of excitotoxic brain damage, or (2) disease processes which involve NMDA receptor hypofunction, such as schizophrenia.

The methods and compositions may comprise (1) an alpha-2 adrenergic agonist to be administered on its own, such as for treatment of schizophrenia, or (2) an alpha-2 adrenergic agonist in combination with an NMDA receptor antagonist, for purposes such as reducing excitotoxic neuronal damage or treating neuropathic pain. When an amount of an alpha-2 adrenergic receptor agonist sufficient to suppress or prevent the neurotoxic side effects of an NMDA antagonist is used, this permits the NMDA antagonist to be used more safely for a number of therapeutic purposes including: 1) protecting against neuronal degeneration such as occurs in acute CNS injury syndromes such as stroke, epilepsy and CNS trauma, and chronic neurodegenerative diseases such as Alzheimer's disease, amyotrophic lateral sclerosis, AIDS dementia, Parkinson's disease and Huntington's chorea; 2) analgesic therapy for alleviating neuropathic pain; 3) preventing the development of tolerance to, dependence on, and craving for addictive drugs, including opiate analgesics, cocaine, anxiolytics, and sedative hypnotics, such as benzodiazepines and barbiturates. In some cases, such as the treatment of neuropathic pain, combining an alpha-2 adrenergic agonist with an NMDA antagonist may increase both the safety and efficacy of the treatment. Similarly, combining both of these classes of agents with an opiate analgesic for treatment of other forms of pain may increase both the safety and efficacy of the treatment.

The Applicants have further recognized that, in view of the correlations between (1) pathological brain changes caused by NRH which has been artificially induced by NMDA antagonist drugs, and (2) pathological brain changes caused by NRH which occurs endogenously as a causative or aggravating factor in schizophrenia, a number of other drugs which can block the neurotoxic side effects caused by NMDA antagonists such as PCP or MK-801 are also likely to be able to reduce, retard, or prevent the pathological brain changes that occur in schizophrenia. As noted above, such drugs include (1) anticholinergic drugs which block the muscarinic class of cholinergic receptors, such as scopolamine, atropine, benztropine, trihexyphenidyl, biperiden, procyclidine, benactyzine or diphenhydramine; see Olney et al 1991, and U.S. Pat. No. 5,034,400 (Olney 1991); (2) certain types of barbiturates, such as secobarbitol, which act as "direct GABA agonists" at $GABA_A$ receptors (Olney et al 1991); and, (3) benzodiazepines that potentiate the action of GABA at $GABA_A$ receptors (Olney et al 1991); and, (4) certain types of drugs that interact primarily with sigma receptor complexes which are modulated by neuropeptide Y (Olney and Farber 1995).

In addition to the foregoing classes of drugs, the Applicants have also recently discovered that non-NMDA antagonist drugs which can penetrate the BBB and block the KA and/or QUIS/AMPA classes of EAA receptors. Examples include NBQX (which is 2,3-dihydroxy-6-nitro-7-sulfamoylbenzo(F)quinoxaline; see Sheardown et al 1989 and 1990) and GYKI 52466 (which is 1-(amino-phenyl)-4-methyl-7,8-methylendioxy-5H-2,3-benzodiazepine; see Tarnawa et al 1990), which, as the Applicants have recently discovered, apparently can also block the neurotoxic side effects of NMDA antagonist drugs such as MK-801. These results were demonstrated by the Applicants in in vivo tests on adult rats, comparable to the tests described in Example 1.

Accordingly, based on the Applicants' findings described herein, drugs from any of these classes that penetrate mammalian blood-brain barriers in sufficient quantity, and that have sufficient levels of potency at the relevant classes of neuronal receptors listed above, are believed to be likely to reduce, retard, or prevent the pathological brain changes that occur in schizophrenia if administered as soon as practical after the onset of signs or symptoms, and are good candidates for screening and evaluation as described herein. One such screening assay using lab animals involves testing candidate compounds using chronic administration, to see whether such candidate drugs can prevent pathological brain changes associated with long-term administration of low dosages of an NMDA antagonist, as described in Example 5.

It is also believed by the Applicants that treatments, involving drugs referred to herein, which interact with more than one class of neuronal receptor, may prove to be optimal for suppressing and preventing the wide range of signs, symptoms, and pathological brain alterations that are manifested in various cases of schizophrenia. Such multi-receptor treatments may be carried out by administering combinations of drugs, wherein each drug has a specific receptor affinity, or by administering certain drugs (typically called "broad-spectrum" drugs) that have affinity for more than one type of neuronal receptor.

In summary, the Applicants have discovered and disclosed a method for treating schizophrenia mediated by endogenously occurring NMDA receptor hypofunction (NRH), comprising the step of administering, to a human patient in need thereof, a pharmacologically acceptable drug (or combination of drugs) which penetrate(s) mammalian blood-brain barriers in an amount effective in inhibiting adverse neurological effects caused by NMDA receptor hypofunction, wherein the drug (or combination of drugs) is administered on a preventive basis as soon as practical after appearance of signs and symptoms of schizophrenia, in order to prevent or retard permanent brain alterations that would be caused by NMDA receptor hypofunction, in the absence of the drug(s).

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLES

EXAMPLE 1: PROTECTION AGAINST MK-801 SIDE EFFECTS BY α2 AGONISTS

This example illustrates the neurotoxic effects of the NMDA antagonist MK-801 (dizocilpine) and the protective effect of various alpha-2 adrenergic receptor agonists.

Adult female rats received MK-801 (0.5 mg/kg) injected subcutaneously (sc), together with one of several test agents (clonidine, xylazine, guanabenz, p-iodoclonidine) injected into the intraperitoneal (ip) region at various doses. Control animals received MK-801 (0.5 mg/kg sc) and either dimethyl sulfoxide (DMSO) or saline, the vehicles used to dissolve the test agents. For each test agent, at least 17 rats were used and at least four doses tested. The dose of MK-801 employed has been shown previously to consistently induce in treated rats a fully developed neurotoxic reaction consisting of acute vacuole formation in the majority of pyramidal neurons in layers III and IV of the posterior cingulate (PC) and retrosplenial (RS) cortices.

The rats were sacrificed four hours after treatment, and brain tissue from the PC/RS region was histopathologically evaluated by previously described methods using double-blinded techniques (Olney et al 1991). The number of vacuolated PC and RS neurons were counted on each side of the brain at a rostrocaudal level immediately posterior to where the corpus callosum ceases decussating across the midline (approximately 5.6 mm caudal to Bregma; Paxinos & Watson, *The Rat Brain in Stereotaxic Coordinates, 2d Ed.,* 1986). In previous tests (Farber et al 1993), the Applicants had found that the toxic reaction approaches maximal severity at this level and does not vary much in severity from one animal to another. Percentage reduction in neurotoxicity was calculated by dividing the mean number of vacuolated neurons in a given experimental group, by the mean number in the control animals which received MK-801 but no α2 agonist; the result was subtracted from one and multiplied by 100 to generate a percentage figure. Linear regression analysis was used to determine an $ED_{50}$ (i.e., the dose of a given α2 agonist that reduced the mean number of vacuolated neurons to 50% of the control mean); the 25th and 75th percentiles were also recorded, to indicate confidence limits.

All control animals developed a neurotoxic reaction to MK-801 (mean number of vacuolated neurons per section= 223±10.5 SEM; n=26).

Of the various $\alpha 2$ agents tested, clonidine was the most potent at preventing the neurotoxic reaction. From 0.01 to 1.0 mg/kg, it dose-dependently suppressed MK-801 induced neurotoxicity ($ED_{50}$=0.044 mg/kg). Xylazine (1–5 mg/kg) was the least potent in preventing the reaction ($ED_{50}$=2.4 mg/kg). Guanabenz ($ED_{50}$=0.21 mg/kg) and p-iodoclonidine ($ED_{50}$=1.3 mg/kg) conferred protection with a potency intermediate between the other two agents. These results are summarized in Table 1.

TABLE 1

Efficacy of alpha-2 Adrenergic Agonists in Blocking MK-801 Neurotoxicity

| Test Compound | $ED_{50}$ (mg/kg, ip) | Confidence Limits (25th & 75th percentiles) |
| --- | --- | --- |
| Clonidine | 0.044 | (0.0088–0.22) |
| Guanabenz | 0.21 | (0.13–0.33) |
| p-Iodoclonidine | 1.3 | (0.29–5.8) |
| Xylazine | 2.4 | (1.4–4.2) |

EXAMPLE 2: USE OF $\alpha 2$ ANTAGONISTS TO CONFIRM $\alpha 2$ RECEPTOR ROLE

The following example confirms that the neuroprotective effects provided by $\alpha 2$ agonists are mediated through the $\alpha 2$ receptor, rather than through cross-reactivity at some other receptor or through some other mechanism, by showing that these neuroprotective effects are blocked by alpha-2 adrenergic antagonists.

Adult female rats received MK-801 (0.5 mg/kg sc) plus a combination of various doses of the $\alpha 2$ agonist xylazine (ip) and a fixed dose of yohimbine (1 mg/kg ip), an antagonist drug that selectively blocks activation of $\alpha 2$ receptors. The brains were processed and the severity of damage assessed as described in Example 1. Results were analyzed by analysis of variance (ANOVA) where the dose of xylazine was the covariate and the presence of yohimbine served as the classification (treatment) variable. The homogeneity of slopes assumption was tested by determining whether there was a significant interaction between the covariate and the treatment variable.

Figure 2:
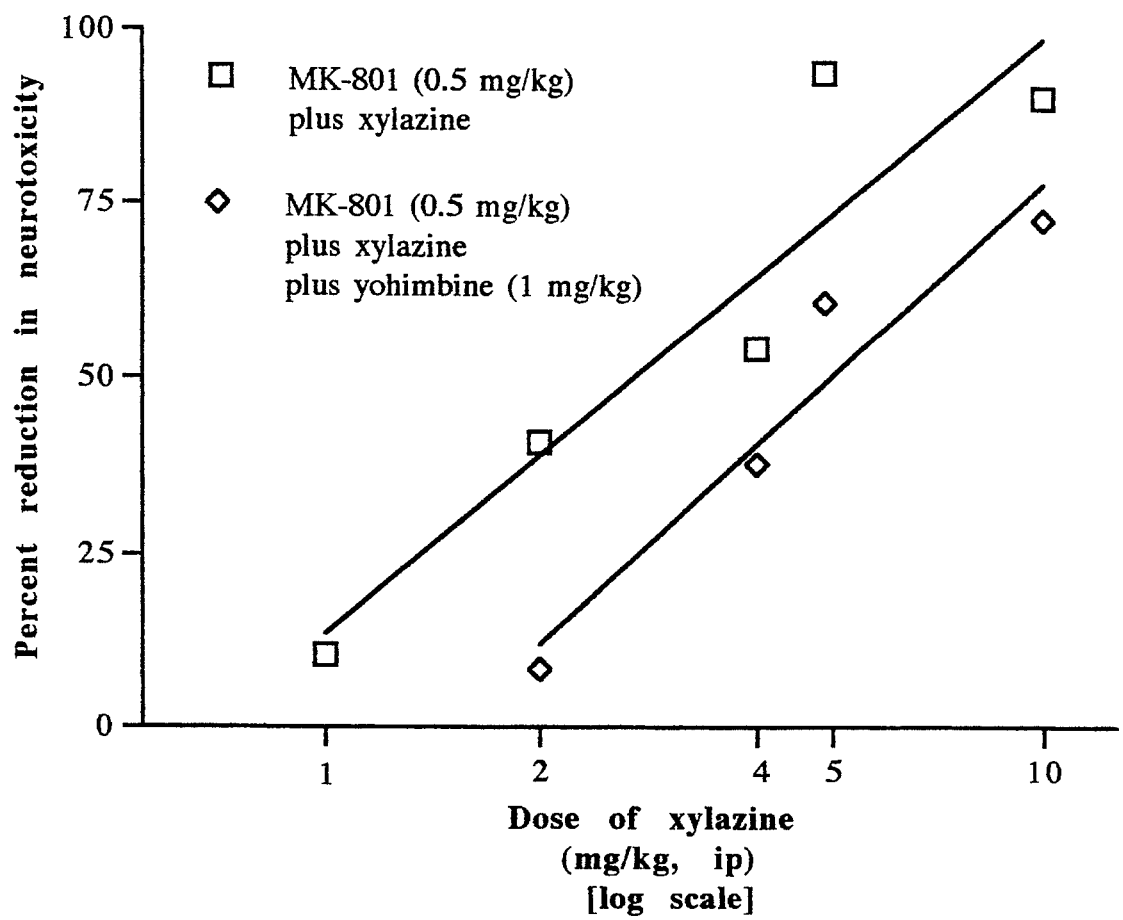
FIG. 2 illustrates the competitive inhibition by yohimbine (an α2 antagonist) of xylazine's protective effect against MK-801 neurotoxicity, to confirm that the α2 receptor is involved in NRH-mediated neurotoxicity.

When a fixed dose of yohimbine (1 mg/kg ip) was administered together with various doses of xylazine to MK-801-treated rats, the yohimbine significantly interfered with xylazine's protection [$F(1,42)$=9.40, $p$=0.004] and shifted the blocking curve to the right, as shown in FIG. 2. Data points in FIG. 2 represent the percent reduction in neurotoxicity, calculated as described in Example 1. This effect is consistent with a competitive interaction between xylazine and yohimbine at alpha-2 adrenergic receptor sites. A similar shifting of the curve to the right was seen in preliminary experiments with a small number of animals treated with the yohimbine antagonist (1 mg/kg ip) combined with clonidine (n=4), or in animals treated with a different $\alpha 2$ antagonist, rauwolscine (5 mg/kg ip), and clonidine (n=4).

The present finding that $\alpha 2$ agonists block the neurotoxicity of NMDA antagonists suggests that $\alpha 2$ receptors are a critical component of the circuitry through which the neurotoxic reaction is mediated. Although the practical and effective use of the invention disclosed herein does not depend upon any hypothesized molecular or cellular mode of action, it is believed that norepinephrine functions in a manner comparable to GABA in various neuronal circuits, to inhibit the release of an excitatory transmitter (perhaps ACh, as suggested by the circuit diagram in FIG. 1) that is instrumental in producing the neurotoxic reaction. Blockade of NMDA receptors by MK-801 abolishes both the inhibitory action of GABA and norepinephrine, thus allowing excessive release of excitatory transmitter as the proximal mechanism triggering the neurotoxic reaction. Administration of an alpha-2 agonist restores inhibitory control and prevents excessive release of excitatory transmitter, thereby preventing the neurotoxic reaction.

EXAMPLE 3: NON-INTERFERENCE WITH THE USEFUL EFFECTS OF NMDA ANTAGONISTS

Several tests were performed to ensure that when an $\alpha 2$ agonist is administered together with an NMDA antagonist, the $\alpha 2$ agonist will not interfere with the desirable neuroprotective properties of the NMDA antagonist.

These experiments were performed using segments of chick embryo retina. This is a widely used model for studying the production and prevention of excitotoxic phenomena, since it is simple and inexpensive. Chick tissue is used, since it tends to provide a better model of adult mammalian tissue than embryonic or juvenile mammalian tissue. Unlike newborn mammals, which are usually blind at birth, baby chicks can see quite well as soon as they emerge from the shell, and the NMDA receptors in chick retinal tissue are fully mature and functional.

In these tests, NMDA was introduced into the incubation medium in a concentration (40 µM) sufficient to produce a fully developed excitotoxic lesion within 30 min, displaying acute degeneration and necrosis of the majority of neurons in the inner layers of the retina. The control retinas were incubated with NMDA alone, and experimental retinas were incubated with NMDA plus MK-801 in sufficient concentration (500 nM) to completely block the NMDA receptors and prevent excitotoxic lesions from developing. Additional experimental retinas were incubated with NMDA plus MK-801 plus either of two $\alpha 2$ agonists, clonidine or xylazine, in a wide range of concentrations (500 nM to 100 µM).

The results were that all retinas incubated in NMDA alone (n =6) had well developed acute lesions affecting the inner neural layers of the retina and extending across the full width of the retina. In contrast, retinas incubated in NMDA plus MK-801, either with or without various concentrations of the $\alpha 2$ agonists clonidine or xylazine, showed no cytopathology (n=6 retinas per treatment condition). Thus, the NMDA antagonist MK-801 completely protected against excitotoxic damage, regardless of whether an $\alpha 2$ agonist was present in the incubation medium. The $\alpha 2$ agonists did not block the useful protective effects of the NMDA antagonist.

EXAMPLE 4: SCREENING OF ANTI-PSYCHOTIC DRUGS FOR PROTECTION AGAINST MK-801 SIDE EFFECTS

After recognizing that a correlation existed between a neurotoxic NRH condition caused by NMDA antagonist drugs, and similar NRH conditions that occur as a disease process in schizophrenic patients, the Applicants decided to screen several drugs that have either proven or putative antipsychotic effects and are considered potentially useful as anti-schizophrenia drugs, to determine whether such drugs would block the neurotoxic side effects of NMDA antagonists such as MK-801.

Several of the antipsychotic agents tested (haloperidol, thioridazine and loxapine) are known to interact with both dopamine receptors and sigma receptors. Two drugs with putative antipsychotic effects (di(2-tolyl)guanidine and rimcazole) are more selective, and have substantial affinity only for sigma receptors. Three others (clozapine, fluperlapine, and olanzapine) are often referred to as "atypical" antipsychotic agents.

In these tests, neurotoxic side effects (measurable as vacuoles and other neuronal damage in PC/RS cortical neurons in rats) were elicited by administering MK-801 to rats, as described in Example 1. Control animals received saline or DMSO, but no anti-psychotic drugs. Test animals were injected ip with an antipsychotic drug, listed above and in Table 2. Vacuoles were counted and data were processed as described in Example 1.

The results, shown in Table 2, indicate that all but one of the compounds tested were active, at varying $ED_{50}$ doses, in protecting against the toxic side effects of NMDA receptor hypofunction (NRH). The single exception was sulpiride, which was inactive; this may have been because the sulpiride was administered only 15 minutes prior to addition of MK-801, and it was subsequently learned by the Applicants that sulpiride apparently takes several hours to penetrate into the CNS.

Since the various agents which were effective in blocking NMDA antagonist neurotoxicity in this study are agents that have either proven or putative antipsychotic activity, these results are consistent with the conclusion that compounds which can block NRH neurotoxicity induced by NMDA antagonist drugs in laboratory animals are also likely to be effective in treating similar types of NRH-related neurotoxicity which occur as a component of idiopathic psychotic illnesses such as schizophrenia.

TABLE 2

EFFECTS OF VARIOUS ANTI-PSYCHOTIC DRUGS IN
PROTECTING AGAINST NRH-INDUCED VACUOLES

| TEST COMPOUND | $ED_{50}$ (MG/KG ip) | CONFIDENCE LIMITS (25th & 75th percentiles) |
|---|---|---|
| Olanzapine | 1.4 | (0.7–2.6) |
| Fluperlapine | 2.3 | (1.5–3.5) |
| Clozapine | 3.2 | (1.1–9.7) |
| Haloperidol | 5.1 | (2.4–10.9) |
| Rimcazole | 17.8 | (8.9–35.6) |
| Di(2-tolyl) guanidine | 22.2 | (15.0–33.3) |
| Loxapine | 23.6 | (3.9–140.6) |
| Thioridazine | 55.3 | (25.0–122.2) |
| Amoxapine | 75.0 | (55.7–100.9) |
| Sulpiride | >200.0 | Inactive |

EXAMPLE 5: ADDITIONAL TESTS TO CONFIRM THE LINK BETWEEN NRH AND SCHIZOPHRENIA

Several additional tests were carried out to explore the correlation between NMDA receptor hypofunction (NRH) and schizophrenia. In one set of tests, minipumps were implanted subcutaneously in a number of rats, to continuously administer MK-801 at a low dosage (83 µg/kg/hour) for 5 days. The dose delivered on any single day was not enough to kill neurons if delivered in a single bolus; however, continuous slow delivery of the drug at these dosages over a prolonged period of time resulted in a relatively widespread pattern of evolving disseminated brain damage primarily affecting certain limbic brain regions that also have been reported to show pathological changes in the brains of schizophrenic humans autopsied after death.

This result provides yet another link which connects schizophrenia to chronic NRH as a causative mechanism.

In addition, this subchronic delivery approach provides a model that mimics the way in which NMDA receptor hypofunction can gradually and insidiously damage the brain in schizophrenia. This laboratory model can be used to compare the efficacy of candidate α2 agonist drugs (or other classes of drugs) in preventing the damage caused by schizophrenia.

EXAMPLE 6: TESTS SHOWING INVOLVEMENT OF SIGMA, MUSCARINIC, AND NON-NMDA RECEPTORS IN NRH TOXICITY

A set of tests was carried out by the Applicants, to help elucidate the role of various neuronal systems in the toxic side effects caused by NRH. In these tests, combinations of several receptor agonists were microinjected into the cingulate cortex (this type of direct injection into the brain avoided problems of limited permeability through blood-brain barriers). These test drugs included (1) (+)SKF-10, 047, an agonist that stimulates activity at sigma receptors; (2) carbachol, an agonist that stimulates activity at muscarinic-type acetylcholine receptors; and (3) kainic acid, an agonist which stimulates non-NMDA glutamate receptors. In some test animals, only one of these drugs was injected. In other animals, various combinations of two drugs were injected (mixed together in a "cocktail"). In still other animals, all three drugs were injected, mixed together.

In animals injected with all three drugs, a neurotoxic reaction was found in cingulate cortical neurons, which was identical to the toxic reaction that is caused by subcutaneous administration of MK-801, an NMDA antagonist. However, in animals injected with only two (or only one) of the three drugs, no such toxic reaction was found.

These results indicate that NMDA antagonist neurotoxicity involves excessive activation of all three of these receptor systems (i.e., sigma receptors, muscarinic-type cholinergic receptors, and non-NMDA glutamate receptors). These results helped establish the neuronal circuitry that is described in the Background section and shown in schematic form in FIG. 1.

From the finding that it requires excessive activitation of all three systems for NRH-mediated pathomorphological brain changes to occur, it follows that blockade of any one of these systems would prevent such permanent brain damage. However, the Applicants believe that, in at least some cases, excessive activation of any one or two of these systems may be sufficient to trigger transient mental aberrations, such as hallucinations, from which it follows that for optimal clinical management of psychotic symptoms and mental aberrations in schizophrenia, it may be necessary to block at least two or possibly all three of these receptor systems in some cases.

Thus, there has been shown and described a new and useful means for allowing the safe use of NMDA antagonists for purposes such as preventing excitotoxic brain damage, treating neuropathic pain, and preventing development of tolerance to addictive drugs. There has also been disclosed a new and useful method for treating and preventing schizophrenic brain changes. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Backonja, M., et al, "Response of chronic neuropathic pain syndromes to ketamine: a preliminary study," *Pain* 56:51–57 (1994)

Ben-Eliyahu, S., et al, "The NMDA receptor antagonist MK-801 prevents long-lasting non-associative morphine tolerance in the rat," Brain Research 575: 304–308 (1992)

Boast, C. A., "Neuroprotection after brain ischemia: role of competitive NMDA antagonists," Neurology and Neurobiology 46: 691–698 (1988)

Brosnan-Watters, G., et al, "High dose MK-801 kills neurons in a single brain region and chronically impairs memory," Soc Neurosci Abst 20: 1217 (1994)

Carter, C, et al, "Ifenprodil and SL 82.0715 as cerebral anti-ischemic agents. II. Evidence for N-methyl-D-aspartate receptor antagonist properties," J Pharmacol Exptl Ther 247: 1222–1232 (1988)

Choi, D. W., "Glutamate neurotoxicity and diseases of the nervous system," Neuron 1: 623–634 (1988)

Choi, D. W., "Excitotoxic cell death," J Neurobiol 23: 1261–1276 (1992)

Corso, T, et al, "Ethanol-induced degeneration of dentate gyrus, entorhinal cortex and other olfactory related areas in rat: effects of co-administration of MK-801, DNQX, or nimodipine," Soc Neurosci Abst 18: 540 (1992)

Corso, T. D., et al, "Neuron necrotizing properties of phencyclidine," Soc Neurosci Abst 20: 1531 (1994)

Dahlstrom, "The Adrenergic Nervous System," pp 11–14 in Encyclopedia of Neuroscience, G. Adelman, ed. (Birkhauser, Boston, 1987)

Danzebrink, R. M. and Gebhart, G. F., "Antinociceptive effects of intrathecal adrenoceptor agonists in a rat model of visceral nociception," J Pharmacol Exp Therapeutics 253: 698–705 (1990)

Davar, G, et al, "MK-801 blocks the development of thermal hyperalgesia in a rat model of experimental painful neuropathy," Brain Res 553: 327–330 (1991)

Dikinson, K. E. J. and Lefkowitz, R. J., "Adrenergic Receptors," pp. 14–16 in Encyclopedia of Neuroscience, G. Adelman, ed. (Birkhauser, Boston, 1987)

Doze, V. A., et al, "Dexmedetomidine produces a hypnotic-anesthetic action in rats via activation of central alpha-2 adrenoceptors," Anesthesiology 71: 75–79 (1989)

Ellison, G. and Switzer, R. C., "Dissimilar patterns of degeneration in brain following four different addictive stimulants," Neuroreport 5: 17–20 (1993)

Fagg, G. E., et al, "CGP 37849 and CGP 39551: novel competitive NMDA receptor antagonists with potent oral anticonvulsant activity," Prog Clin Biol Res 361: 421–7 (1990)

Farber, N. B., et al, "Antipsychotic drugs block phencyclidine receptor-mediated neurotoxicity," Biol Psychiatry 34: 119–121 (1993)

Ferkany, J. W., et al, "Pharmacological profile of NPC 12626, a novel, competitive NMDA receptor antagonist," J Pharmacol Exp Ther 250: 100–109 (1989)

Ferkany, J. W., et al, "Pharmacological profile of NPC 17742 [2R,4R,5S-(2-amino-4,5-(1,2-cyclohexyl)-7-phosphonoheptanoic acid)], a potent, selective and competitive N-methyl-D-aspartate receptor antagonist," J Pharmacol Exp Ther 264: 256–64 (1993)

Fix, A. S., et al, "Light and electron microscopic evaluation of neuronal vacuolization and necrosis induced by the non-competitive NMDA antagonist MK-801 in the rat retrosplenial cortex," Exp Neurol 123: 204–215 (1993)

Freedman, R., et al, "Clonidine treatment of schizophrenia: Double-blind comparison to placebo and neuroleptic drugs," Acta Psych. Scand. 65: 35–40 (1982)

Goodman and Gilman, eds., The Pharmacological Basis of Therapeutics (Macmillan, NY, 1990)

Green, J. J. and Cordes, D. H., "Transdermal clonidine therapy and nicotine withdrawal," West J Med 151: 79–80 (1989)

Grotta, J., "Safety and Tolerability of the Glutamate Antagonist CGS 19755 in Acute Stroke Patients," Stroke 25: 255 (1994)

Hargreaves, R. J., et al, "Competitive as well as uncompetitive NMDA receptor antagonists affect cortical neuronal morphology and cerebral glucose metabolism," Neurochem Research 18: 1263–1269 (1993)

Herrling, P. L. "D-CPPene (SDZ EAA 494), a competitive NMDA antagonist: Results from animal models and first results in humans," Neuropsychopharmacology 10, No 3S/Part 1: 591S (1994)

Horvath, Z. and Buzsaki, G, "MK-801-Induced Neuronal Damage in Normal Rats," Soc Neurosci Abst 19: 354 (1993)

Javitt, D. C. and Zukin, S. R., "Recent Advances in the Phencyclidine Model of Schizophrenia," Am J Psychiat 148: 1301–1308 (1991)

Jimerson, D. C., et al, "Preliminary trial of the noradrenergic agonist clonidine in psychiatric patients," Biol. Psychiatry 14: 45–57 (1980)

Kemp, J. A., et al, "Non-competitive antagonists of excitatory amino acid receptors," TINS 10: 294–299 (1987)

Ko, G. N., et al, "Acute clonidine in schizophrenia," Proc. Amer. Psych. Assn., NR117 (1983)

Kristensen, et al, "The NMDA-receptor antagonist CPP abolishes neurogenic 'wind-up pain' after intrathecal administration in humans," Pain 51: 249–253 (1992)

Krystal, J. H., et al, "Dose-related effects of the NMDA antagonist, Ketamine, in healthy humans," Schizophrenia Research 9: 240–241 (1993)

Lechin, F., et al, "Pharmacomanometrudies of colonic motility as a guide to the chemotherapy of schizophrenia," J. Clin. Pharmacol. 20: 664–671 (1980)

Louis, W. J. et al, "Sites of action of alpha-2 agonists in the brain and periphery," Am. J. Cardiol. 61: 15D–17D (1988)

Luby, E. D., et al, "Model psychoses and schizophrenia," Am J Psych 119: 61–67 (1962)

Magbagbeola, J. A. O. and Thomas, N. A., "Effect of thiopentone on emergence reactions to ketamine anaesthesia," Canad Anaesth Soc J 21: 321–324 (1974)

Mao, J, et al, "Intrathecal MK-801 and local nerve anesthesia synergistically reduce nociceptive behaviors in rats with experimental peripheral mononeuropathy," Brain Res. 576: 254–262 (1992)

Marek, P., et al, "Excitatory amino acid antagonists (kynurenic acid and MK-801) attenuate the development of morphine tolerance in the rat," Brain Research 547: 77–81 (1991)

Marshall, B. E. and Longnecker, D. E., "General anesthetics," pp. 285–310 in The pharmacological Basis of Therapeutics, Goodman, L. S., et al, eds. (Pergamon Press, New York, 1990)

Massieu, L., et al, "A comparative analysis of the neuroprotective properties of competitive and uncompetitive N-methyl-D-aspartate receptor antagonists in vivo: implications for the process of excitotoxic degeneration and its therapy," Neuroscience 55: 883–92 (1993)

McCarthy, D. A., "History of the development of cataleptoid anesthetics of the phencyclidine type," pp. 17–23 in

*PCP (Phencyclidine): Historical and Current Perspectives,* Domino, E. F., ed. (NPP Books, Ann Arbor, Mich., 1981)

Moens, Y. and Fargetton, X., "A comparative study of medetomidine/ketamine and xylazine/ketamine anesthesia in dogs," *The Veterinary Record* 127: 567–571 (1990)

Neugebauer, V., et al, "The clinically available NMDA receptor antagonist memantine is antinociceptive on rat spinal neurones," *NeuroReport* 4: 1259–1262 (1993)

Nevalainen, T., et al, "Evaluation of anesthetic potency of medetomidine-ketamine combination in rats, guinea pigs, and rabbits," *Acta Veterinaria Scandinavica* 85: 139 (1989)

Olney, J. W., "Glutamate," pp 468–470 in *Encyclopedia of Neuroscience,* G. Adelman, ed. (Birkhauser, Boston, 1987)

Olney, J. W., "Excitotoxicity and NMDA receptors," *Drug Dev Res* 17: 299–319 (1989a)

Olney, J. W., et al, "Pathological changes induced in cerebrocortical neurons by phencyclidine and related drugs," *Science* 244: 1360–1362 (1989b)

Olney, J. W., "Excitotoxic amino acids and neuropsychiatric disorders," pp 47–71 in *Annual Review of Pharmacology and Toxicology, Volume* 30, R. George, et al, eds. (Annual Reviews, Inc, Palo Alto, Calif., 1990a)

Olney, J. W., et al, "Cholinotoxic syndromes: Mechanisms and protection," pp 147–162 in *Proceedings of the workshop on convulsions and related brain damage induced by organophosphorus agents, Aberdeen Proving Ground, MD* (U.S. Army, Feb. 1–2, 1990b)

Olney, J. W., et al, "NMDA antagonist neurotoxicity: Mechanism and prevention," *Science* 254: 1515–1518 (1991)

Olney, J. W. and Farber, N. B., "Efficacy of clozapine compared with other antipsychotics in preventing NMDA-antagonist neurotoxicity," *J Clin Psychiatry* 55(9) (suppl. B): 43–46 (1994)

Olney, J. W. and Farber, N. B., *Neuropsychopharmacology* (in press) (1995)

Price, M. T., et al, "Tracing the circuitry that mediates NMDA antagonist neurotoxicity," *Soc Neurosci Abst* 20: 1532 (1994)

Puke, M. J. C. and Wiesenfeld-Hallin, Z., "The differential effects of morphine and the alpha-2-adrenoceptor agonists clonidine and dexmedetomidine on the prevention and treatment of experimental neuropathic pain," *Anesth Analg* 77: 104–109 (1993)

Reich, D. L. and Silvay, G., "Ketamine: an update on the first twenty years of clinical experience," *Can J Anaesth* 36: 186–197 (1989)

Ruffolo, R. R., et al, "Pharmacologic and therapeutic applications of $\alpha 2$-adrenoceptor subtypes," *Annu. Rev. Pharmacol. Toxicol.* 32: 243–279 (1993)

Segal, M., "Overview of drugs used in treating drug-induced dependence," *Int J Addict* 20: 1693–1706 (1985)

Seltzer, Z., et al, "Modulation of neuropathic pain behavior in rats by spinal disinhibition and NMDA receptor blockade of injury discharge," *Pain* 45: 69–75 (1991)

Sershen, H., et al, "Ibogaine reduces preference for cocaine consumption in C57BL/6By mice," *Pharmacol Biochem Behav* 47: 13–19 (1994)

Sheardown, M. J., et al, "NBQX, a specific non-NMDA receptor antagonist, shows neuroprotective effects against cerebral ischemia," abstract published in *Proceedings of the First International Conference on Therapy with Amino Acids and Analogs,* Vienna, Aug. 7–12, 1989.

Sheardown, M. J., et al, "Blockade of AMPA receptors in the CA1 region of the hippocampus prevents ischaemia induced cell death," pp. 245–253 in Krieglstein, J., and Oberpichler, H., eds., *Pharmacology of Cerebral Ischemia* 1990 (Wissenschaftliche Verlagsgesellschaft, Stuttgart, Germany, 1990)

Siegel, E. G., et al, "Investigation of clonidine and lofexidine for the treatment of barbiturate withdrawal in mice," *Vet Hum Toxicol* 27: 503–5 (1985)

Sills, M. A., et al, "CGP 39653: a new N-methyl-D-aspartate antagonist radioligand with low nanomolar affinity in rat brain," *Eur J Pharmacol* 192: 19–24 (1991)

Simpson, G. M., et al, "A preliminary evaluation of the sedative effects of catapres, a new antihypertensive agent, in chronic schizophrenia patients," *J. Clin. Pharmacol.* 7: 221–225 (1967)

Sugarman, A. A., "A pilot study of ST-155 (catapres) in chronic schizophrenia," *J. Clin. Pharmacol.* 7: 226–230 (1967)

Tal, M. and Bennett, G. J., "Dextrorphan relieves neuropathic heat-evoked hyperalgesia in the rat," *Neuroscience Letters* 151: 107–110 (1993)

Tarnawa, I., et al, "GYKI 52466, an inhibitor of spinal reflexes, is a potent quisqualate antagonist," pp. 538–546 in Lubec and Rosenthal (eds.), *Amino Acids: Chemistry, Biology, and Medicine* (ESCOM Science Publishers, Leiden, Netherlands, 1990)

Tassin, J. P., "Norepinephrine and dopamine interactions in prefrontal cortex and their possible roles as neuromodulators in schizophrenia," *J Neural Transm Suppl* 36: 135–62 (1992)

Trendelenburg, A., et al, "Presynaptic a2 autoreceptors in brain cortex: $\alpha 2D$ in the rat and $\alpha 2A$ in the rabbit," *Arch Pharmacol* 348: 35–45 (1993)

Trujillo, K. A. and Akil, H., "Inhibition of morphine tolerance and dependence by the NMDA receptor antagonist MK-801," *Science* 251: 85–87 (1991)

Van Kammen, D. P., et al, "Clonidine treatment of schizophrenia: Can we predict treatment response?" *Psychiatry Research* 27: 297–311 (1989)

Verstegen, J., et al, "Medetomidine/ketamine anaesthesia in cats," *Acta Veterinaria Scandinavica* 85: 117–123 (1989)

Washton, A. M., et al, "Opiate withdrawal using lofexidine, a clonidine analogue with fewer side effects," *J. Clin Psychiatry* 44: 335–337 (1983)

Waterman, A. E., "Influence of premedication with xylazine on the distribution and metabolism of intramuscularly administered ketamine in cats," *Research in Veterinary Science* 35: 285 (1983)

Watkins, J. C., "Excitatory amino acids," pp 37–69 in *Kainic Acid as a Tool in Neurobiology,* McGeer, E., et al, eds. (Raven Press, New York, 1978)

Woolf, C. J., "Recent advances in the pathophysiology of acute pain," *Br J Anaesth.* 63: 139–146 (1989)

Yamamoto, T. and Yaksh, T. L., "Spinal pharmacology of thermal hyperesthesia induced by constriction injury of sciatic nerve. Excitatory amino acid antagonists," *Pain* 49: 121–128 (1992)

Zeigler, D., et al, "Transdermal clonidine versus placebo in painful diabetic neuropathy," *Pain* 48: 403–408 (1992)

We claim:

1. A method for reducing neurotoxic side effects of an NMDA antagonist drug, comprising the step of co-administering, to a mammalian patient receiving an NMDA antagonist drug which has both a therapeutic benefit and a neurotoxic side effect, a second drug which:

a. penetrates mammalian blood-brain barriers;

b. functions as an agonist at alpha-2 adrenergic receptors in central nervous system tissue;

c. acts as a pharmacological safener agent when co-administered with an NMDA antagonist drug, by reducing at least one neurotoxic side effect caused by the NMDA antagonist drug;

and wherein the alpha-2 adrenergic agonist is administered at a therapeutically effective dosage which is effective in reducing neurotoxic side effects of the NMDA antagonist drug.

2. The method according to claim 1 wherein the alpha-2 adrenergic agonist is effective in reducing at least one neurotoxic side effect selected from the group consisting of:

(a) formation of vacuoles in neurons in cerebrocortical or limbic brain regions;

(b) expression of heat shock proteins in cerebrocortical or limbic brain regions;

(c) alteration or loss of mitochondria in neurons;

(d) neuronal death; and, (e) hallucinations and psychotomimetic effects.

3. The method according to claim 1 wherein the NMDA antagonist drug and the alpha-2 adrenergic agonist drug are co-administered to the patient in order to reduce excitotoxic damage to central nervous system tissue caused by ischemia.

4. The method according to claim 1 wherein the NMDA antagonist drug and the alpha-2 adrenergic agonist drug are co-administered to the patient in order to reduce excitotoxic damage to central nervous system tissue caused by hypoxia.

5. The method according to claim 1 wherein the NMDA antagonist drug and the alpha-2 adrenergic agonist drug are co-administered to the patient in order to reduce excitotoxic damage to central nervous system tissue caused by trauma.

6. The method according to claim 1 wherein the NMDA antagonist drug and the alpha-2 adrenergic agonist drug are co-administered to the patient in order to reduce excitotoxic brain damage caused by epileptic seizures.

7. The method according to claim 1 wherein the NMDA antagonist drug and the alpha-2 adrenergic agonist drug are co-administered to the patient in order to reduce neuronal death associated with a chronic neurodegenerative disease which involves excessive activation of neuronal glutamate receptors.

8. The method according to claim 1 wherein the NMDA antagonist drug and the alpha-2 adrenergic agonist drug are co-administered to the patient in order to reduce neuropathic pain.

9. The method according to claim 1 wherein the NMDA antagonist drug and the alpha-2 adrenergic agonist drug are co-administered to the patient in order to suppress development of tolerance to an addictive drug.

10. The method according to claim 1 wherein the alpha-2 adrenergic agonist is selected from the group consisting of clonidine, iodoclonidine, guanabenz, xylazine, medetomidine, tizanidine, rilmenidine, alpha-methyldopa, and alpha-methylnoradrenaline, and pharmacologically acceptable salts thereof.

11. The method according to claim 1 wherein the alpha-2 adrenergic agonist is a highly selective alpha-2 adrenergic agonist which has substantially less activating effects at alpha-1 adrenergic receptors than clonidine.

12. The method according to claim 1 wherein the alpha-2 adrenergic agonist is selected from the group consisting of guanfacine, dexmedetomidine, azepexole, and pharmacologically acceptable salts thereof.

13. The method according to claim 1 wherein the alpha-2 adrenergic agonist has substantially lower hypotensive side effects in humans than clonidine.

14. The method according to claim 13 wherein the alpha-2 adrenergic agonist is selected from the group consisting of lofexidine and guanfacine, and pharmacologically acceptable salts thereof.

15. In the method of administering, to a mammalian patient, an NMDA antagonist drug which offers a therapeutic benefit but which also causes a secondary neurotoxic side effect, an improvement wherein a pharmacologically acceptable alpha-2 adrenergic agonist drug which penetrates mammalian blood-brain barriers is co-administered to the patient, along with the NMDA antagonist drug, in a dosage that is therapeutically effective in reducing the neurotoxic side effect caused by the NMDA antagonist drug.

16. The method according to claim 15 wherein the alpha-2 adrenergic agonist is selected from the group consisting of clonidine, iodoclonidine, guanabenz, xylazine, medetomidine, tizanidine, rilmenidine, alpha-methyldopa, and alpha-methylnoradrenaline, and pharmacologically acceptable salts thereof.

17. The method according to claim 15 wherein the alpha-2 adrenergic agonist is a highly selective alpha-2 adrenergic agonist which has substantially less activating effects at alpha-1 adrenergic receptors than clonidine.

18. The method according to claim 17 wherein the alpha-2 adrenergic agonist is selected from the group consisting of guanfacine, dexmedetomidine, azepexole, and pharmacologically acceptable salts thereof.

19. The method according to claim 15 wherein the alpha-2 adrenergic agonist has substantially lower hypotensive side effects in humans than clonidine.

20. The method according to claim 19 wherein the alpha-2 adrenergic agonist is selected from the group consisting of lofexidine and guanfacine, and pharmacologically acceptable salts thereof.

* * * * *